(12) United States Patent
Niwa et al.

(10) Patent No.: US 10,485,785 B2
(45) Date of Patent: *Nov. 26, 2019

(54) METHOD FOR PRODUCING FINE POWDER AND THE FINE POWDER PRODUCED BY THE SAME

(71) Applicant: Moriroku Chemicals Company, Ltd., Tokyo (JP)

(72) Inventors: Toshiyuki Niwa, Nagoya (JP); Shohei Sugimoto, Nagoya (JP); Kazumi Danjo, Nagoya (JP); Masaaki Nishio, Tokyo (JP); Yasuo Nakanishi, Tokyo (JP); Sakiko Kawamura, Tokyo (JP)

(73) Assignee: Moriroku Chemicals Company, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,935

(22) Filed: May 18, 2015

(65) Prior Publication Data

US 2015/0258066 A1 Sep. 17, 2015

Related U.S. Application Data

(63) Continuation of application No. 13/509,573, filed on Jul. 19, 2012, now Pat. No. 9,044,758.

(51) Int. Cl.
| | | |
|---|---|---|
| *A61J 3/02* | (2006.01) | |
| *B02C 19/18* | (2006.01) | |
| *A61K 9/14* | (2006.01) | |
| *A61K 9/16* | (2006.01) | |
| *C01B 32/50* | (2017.01) | |
| *F25D 3/12* | (2006.01) | |
| *A61K 31/4166* | (2006.01) | |

(52) U.S. Cl.
CPC .......... *A61K 31/4166* (2013.01); *A61K 9/146* (2013.01); *C01B 32/50* (2017.08)

(58) Field of Classification Search
CPC ............. A61J 3/02; A61K 9/14; B02C 19/186
See application file for complete search history.

(56) References Cited

U.S. PATENT DOCUMENTS

| 2,347,464 A * | 4/1944 | Cuno | B02C 19/186 |
| | | | 106/273.1 |
| 2,689,202 A | 9/1954 | Bavley et al. | |
| 5,354,562 A * | 10/1994 | Platz | A61K 9/14 |
| | | | 424/46 |
| 9,044,758 B2 * | 6/2015 | Niwa | B02C 19/186 |

FOREIGN PATENT DOCUMENTS

| CN | 1289199 | 12/2006 | |
| DE | 102004040368 | 2/2006 | |
| DE | 102004040368 B3 * | 2/2006 | ............ B02C 17/20 |
| JP | 2001046899 | 2/2001 | |
| JP | 2002-102682 | 4/2002 | |
| JP | 2002-102729 | 4/2002 | |
| JP | 2002306940 | 10/2002 | |
| JP | 2003001129 | 1/2003 | |
| JP | 2007268403 | 10/2007 | |

OTHER PUBLICATIONS

Fisher, Elizabeth S., "Milling of Active Pharmaceutical Ingredients." Encyclopedia of Pharmaceutical Technology 3 (2006).

* cited by examiner

*Primary Examiner* — Bethany P Barham
*Assistant Examiner* — Peter Anthopolos
(74) *Attorney, Agent, or Firm* — Head, Johnson, Kachigian & Wilkinson, PC

(57) ABSTRACT

Disclosed is a method for producing a fine powder. Two or more kinds of original materials are suspended and liquefied inert gas to form two or more kinds of slurries wherein each slurry contains at least one or more different kinds of original materials. Granular dry ice grinding medium is put into the slurries. The slurries are individually stirred and the original materials are pulverized into submicron-sized or nano-sized particles in the liquefied inert gas. The slurries are thereafter mixed. The liquefied inert gas is vaporized and the granular dry ice is sublimated. A mixture of the particles of the two or more kinds of original materials is recovered.

8 Claims, 39 Drawing Sheets

[Fig. 1]
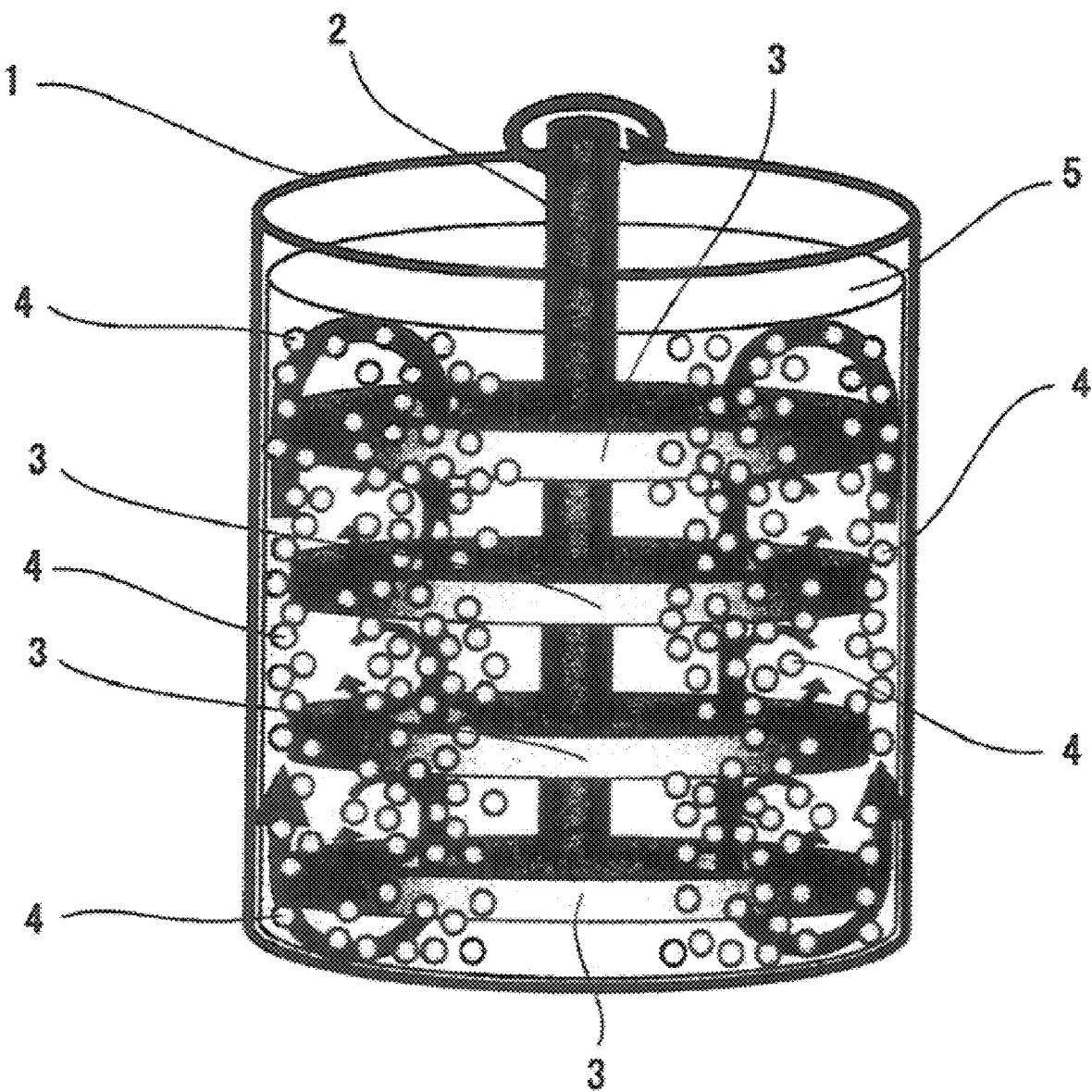

[Fig. 5]
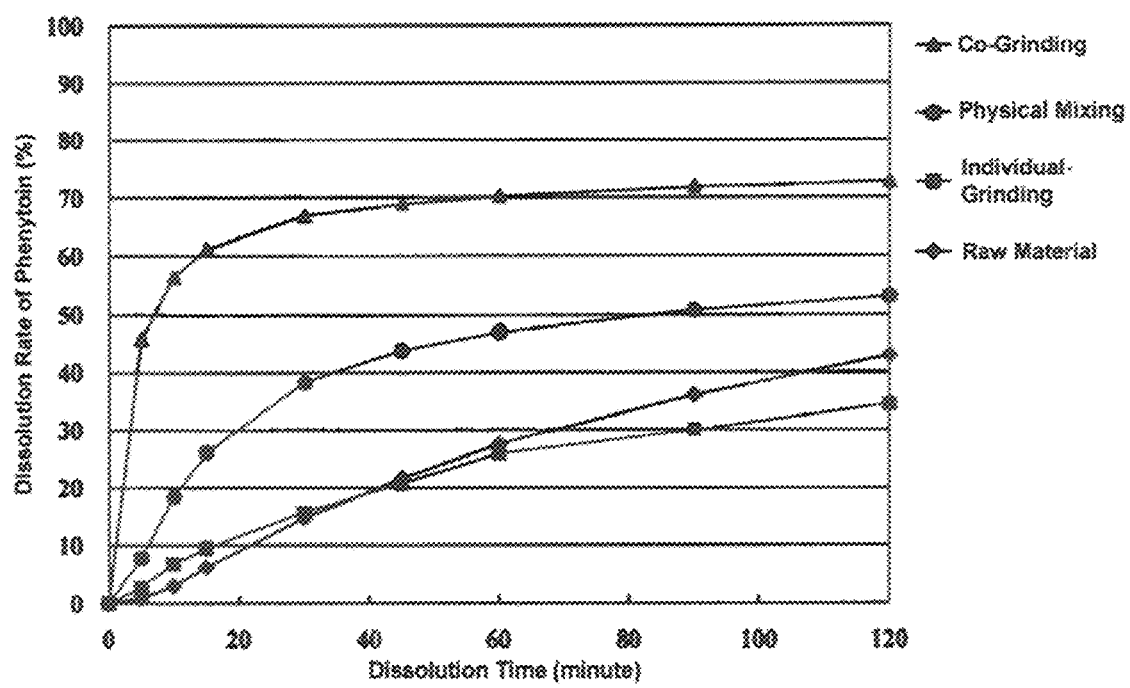
[Fig. 6]
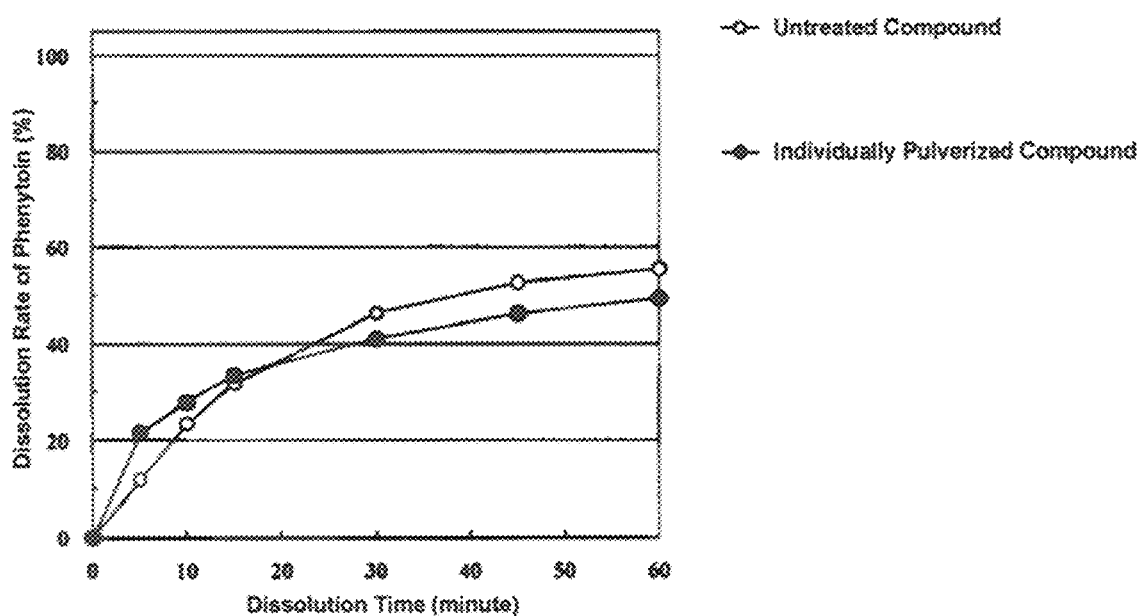

[Fig. 7]
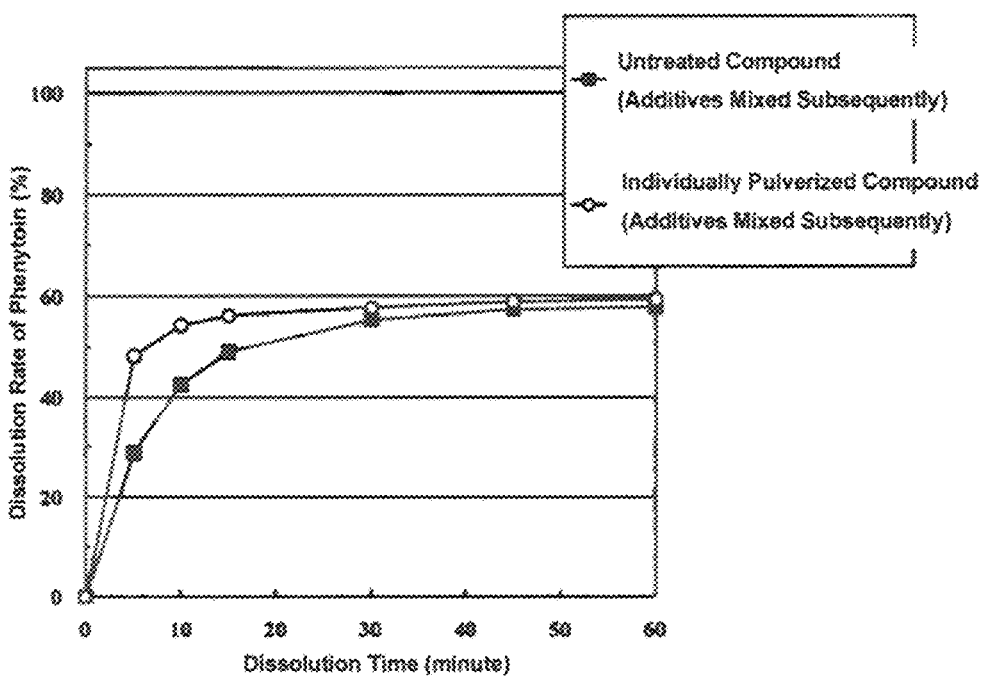
[Fig. 8]
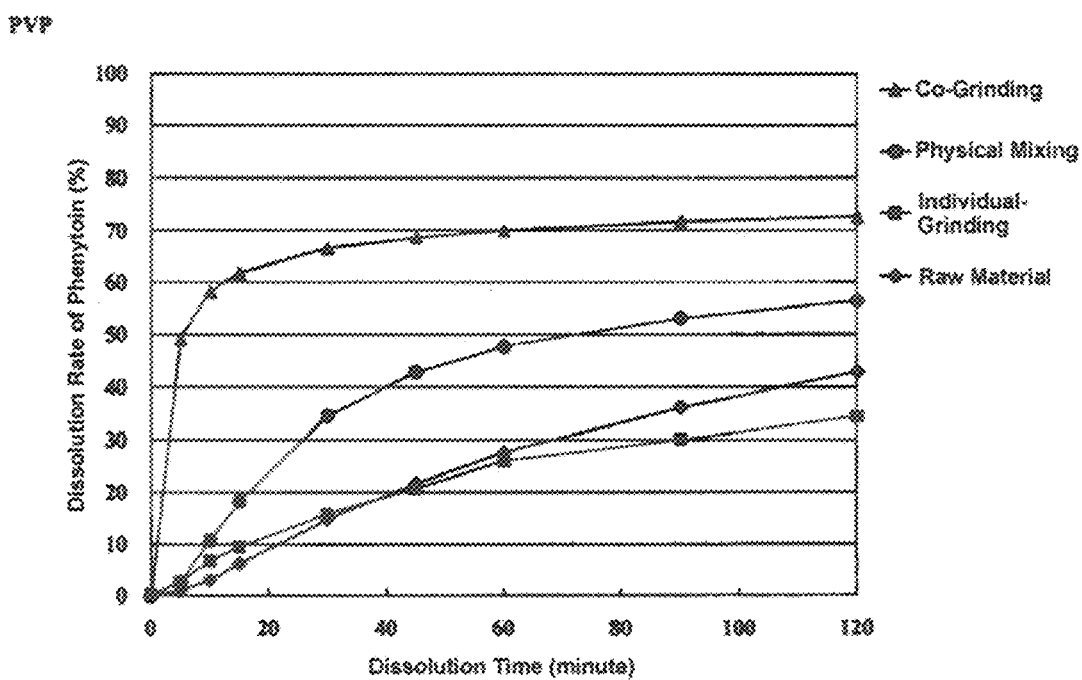

[Fig. 9]
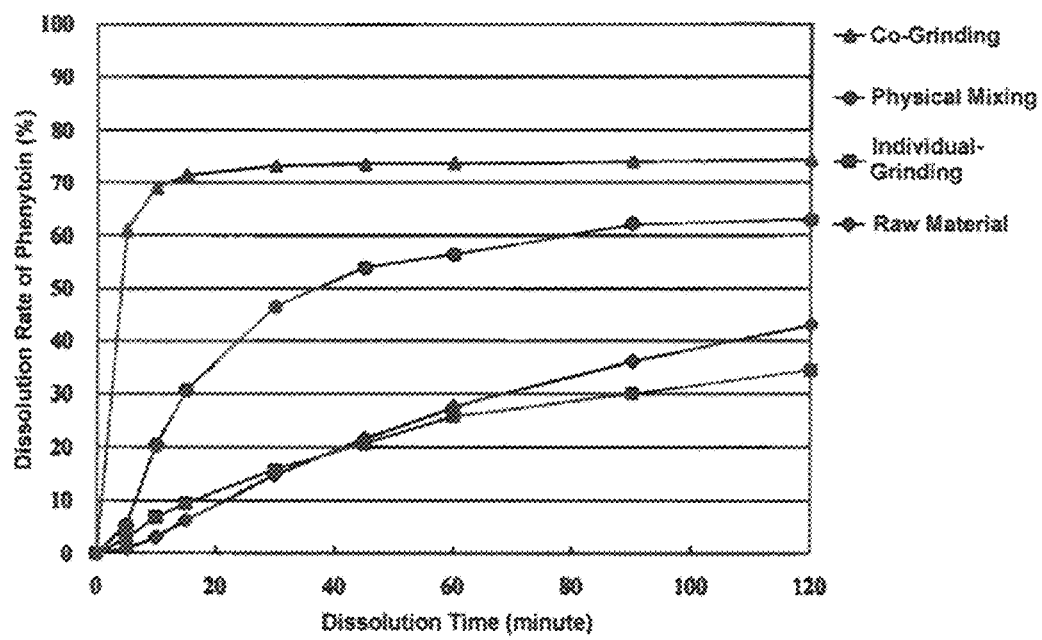
[Fig. 10]
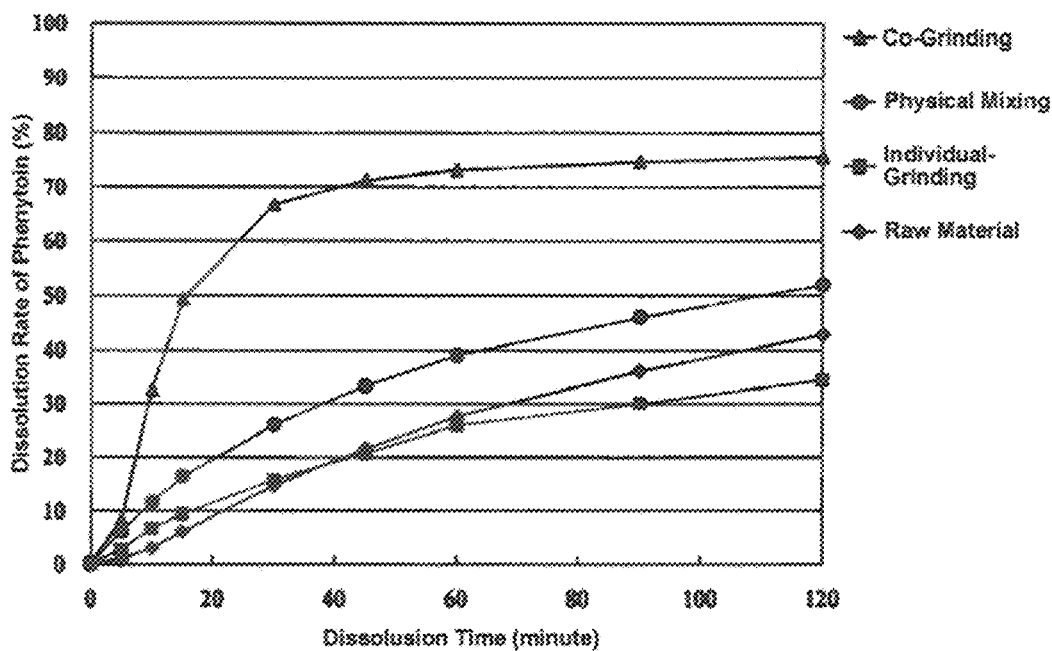

[Fig. 11]
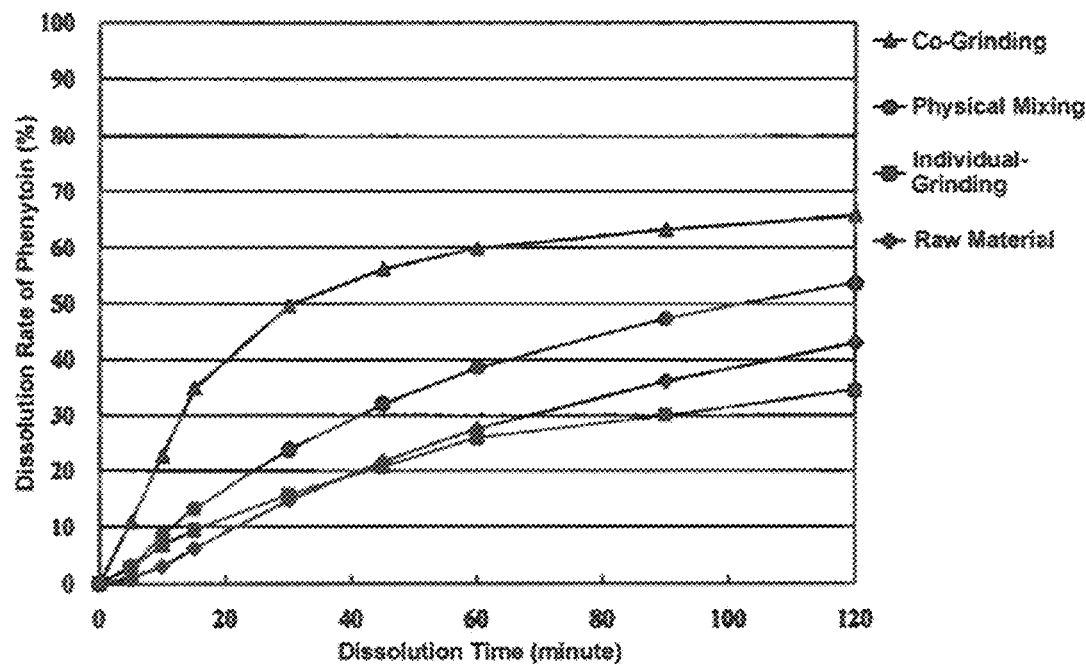
[Fig. 12]
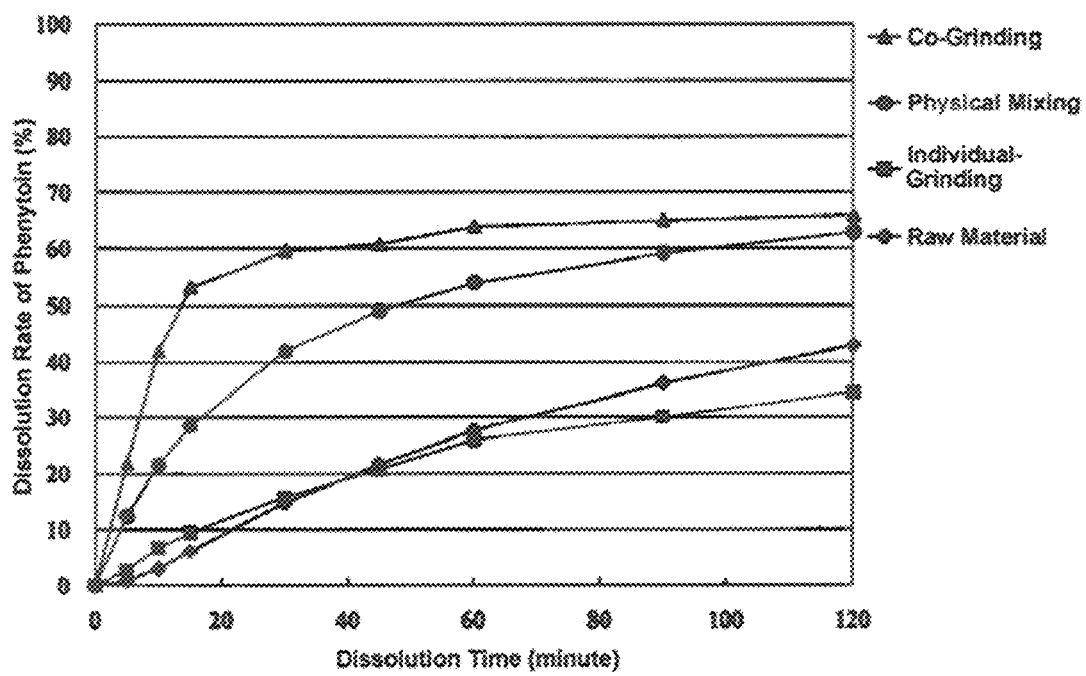

[Fig. 13]
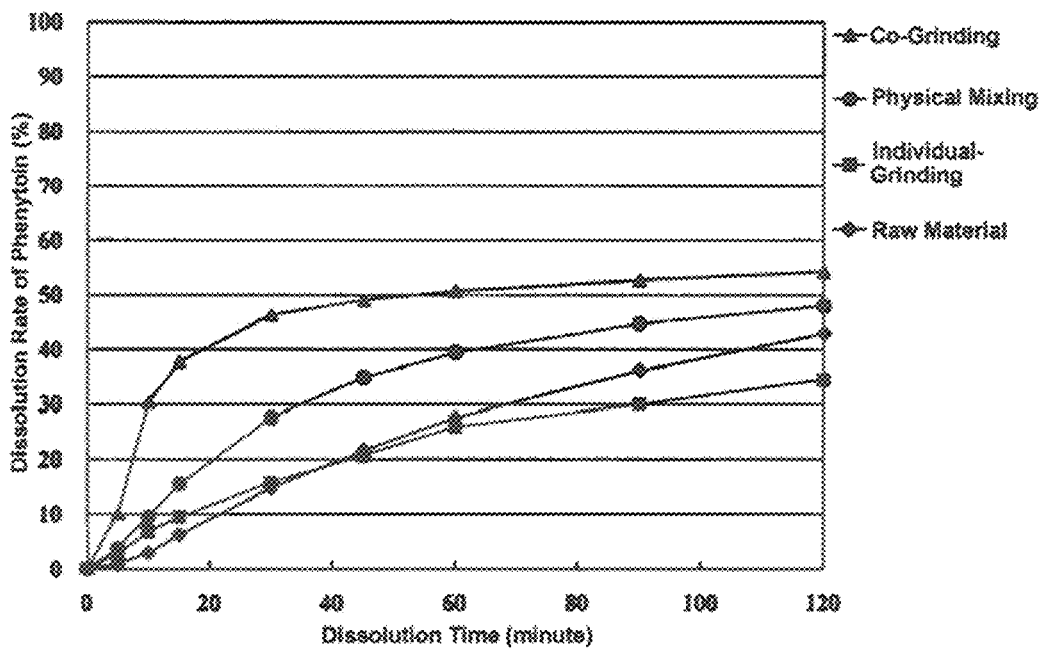
[Fig. 14]
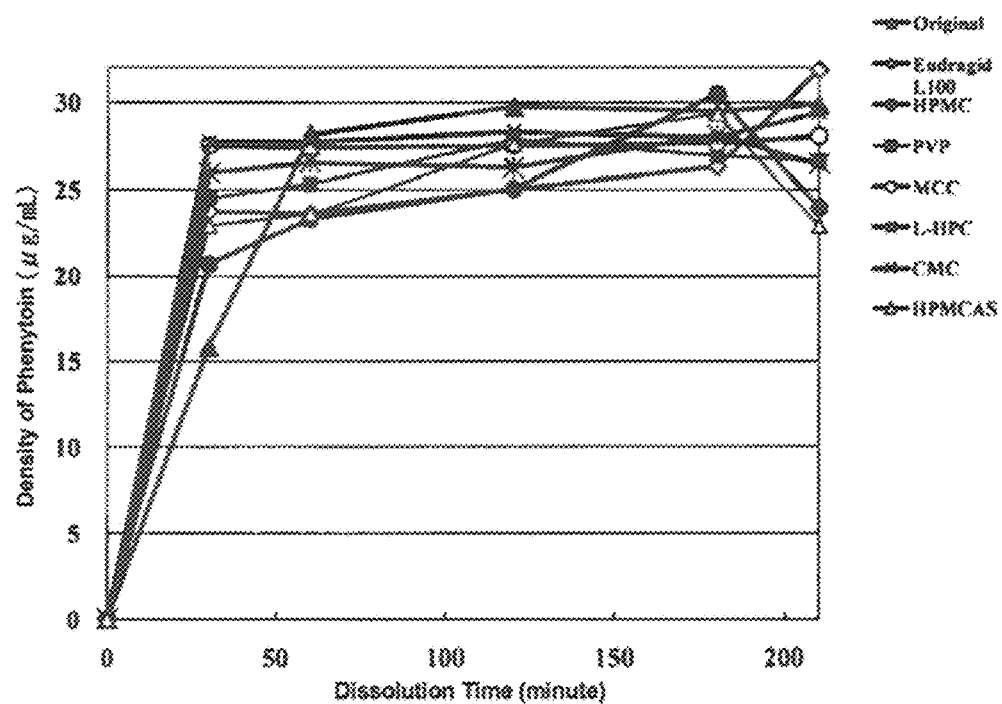

[Fig. 15]
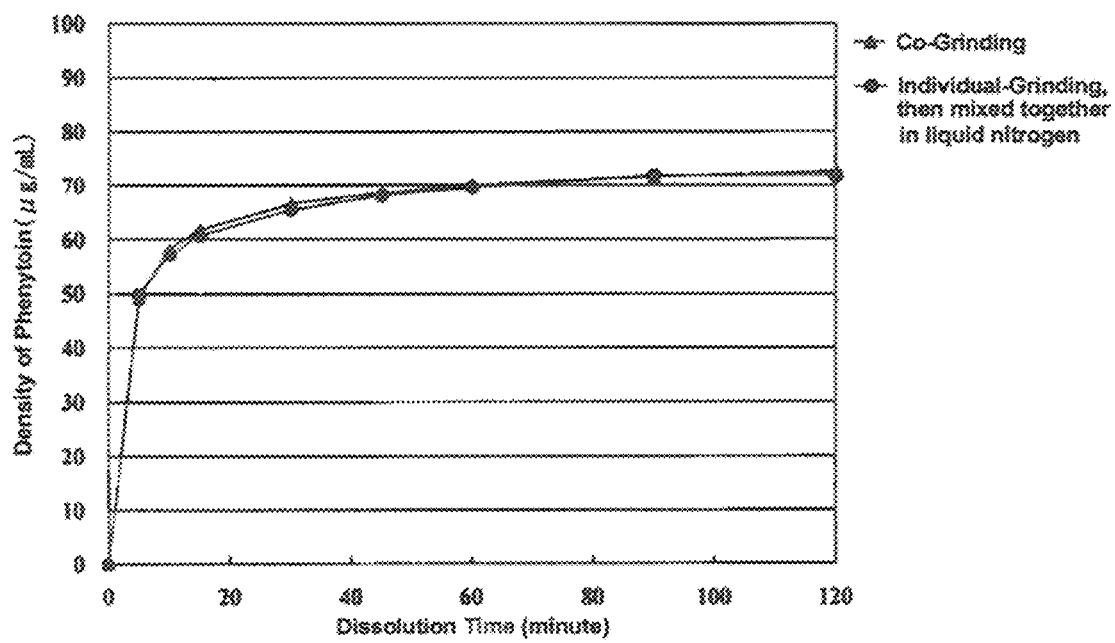
[Fig. 16]
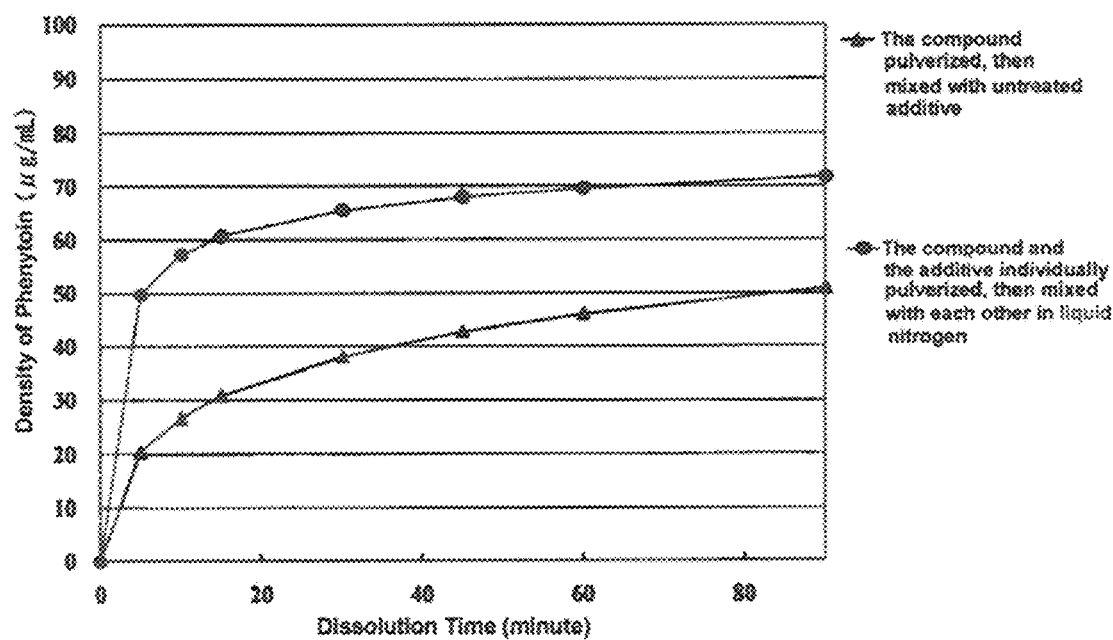

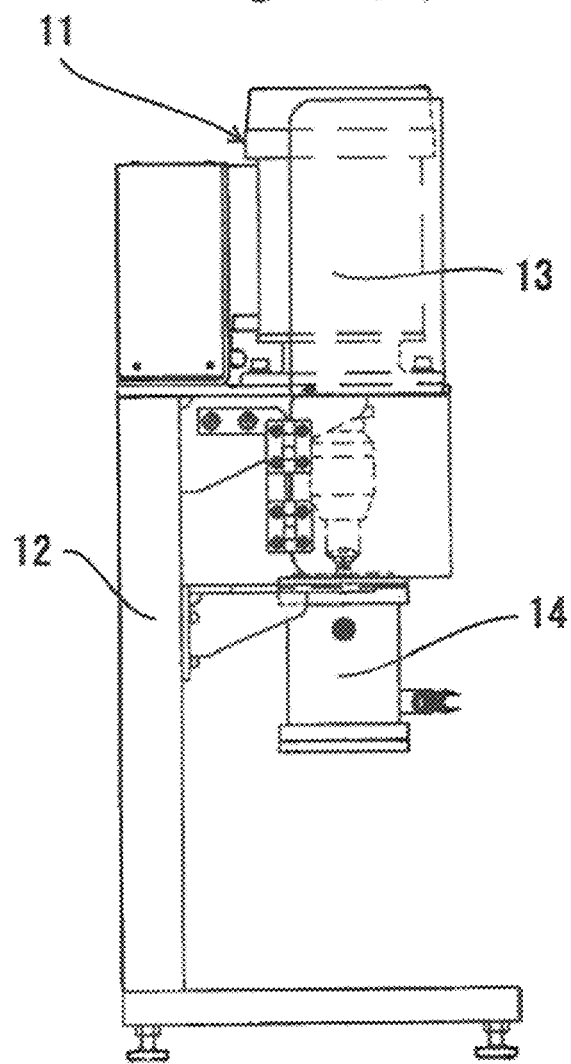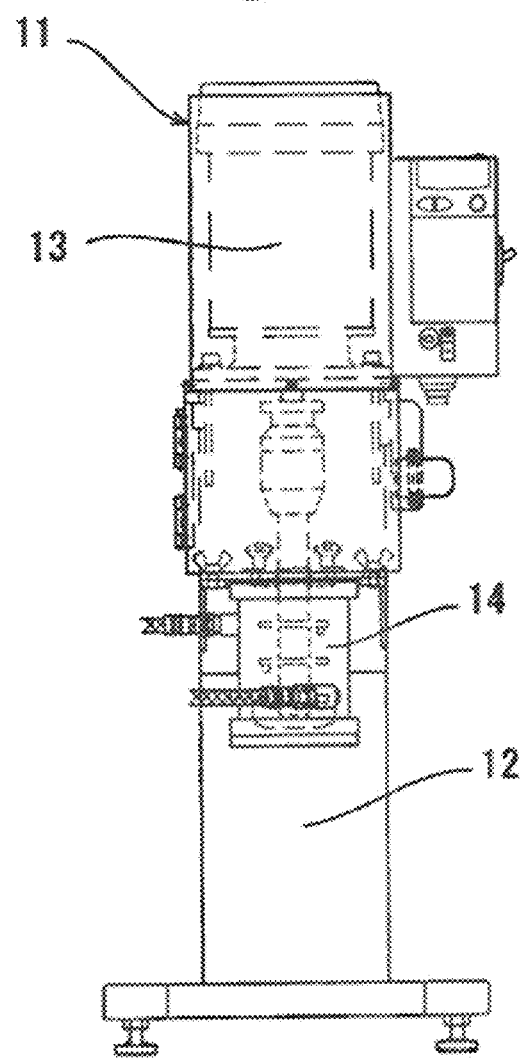

[Fig. 18]
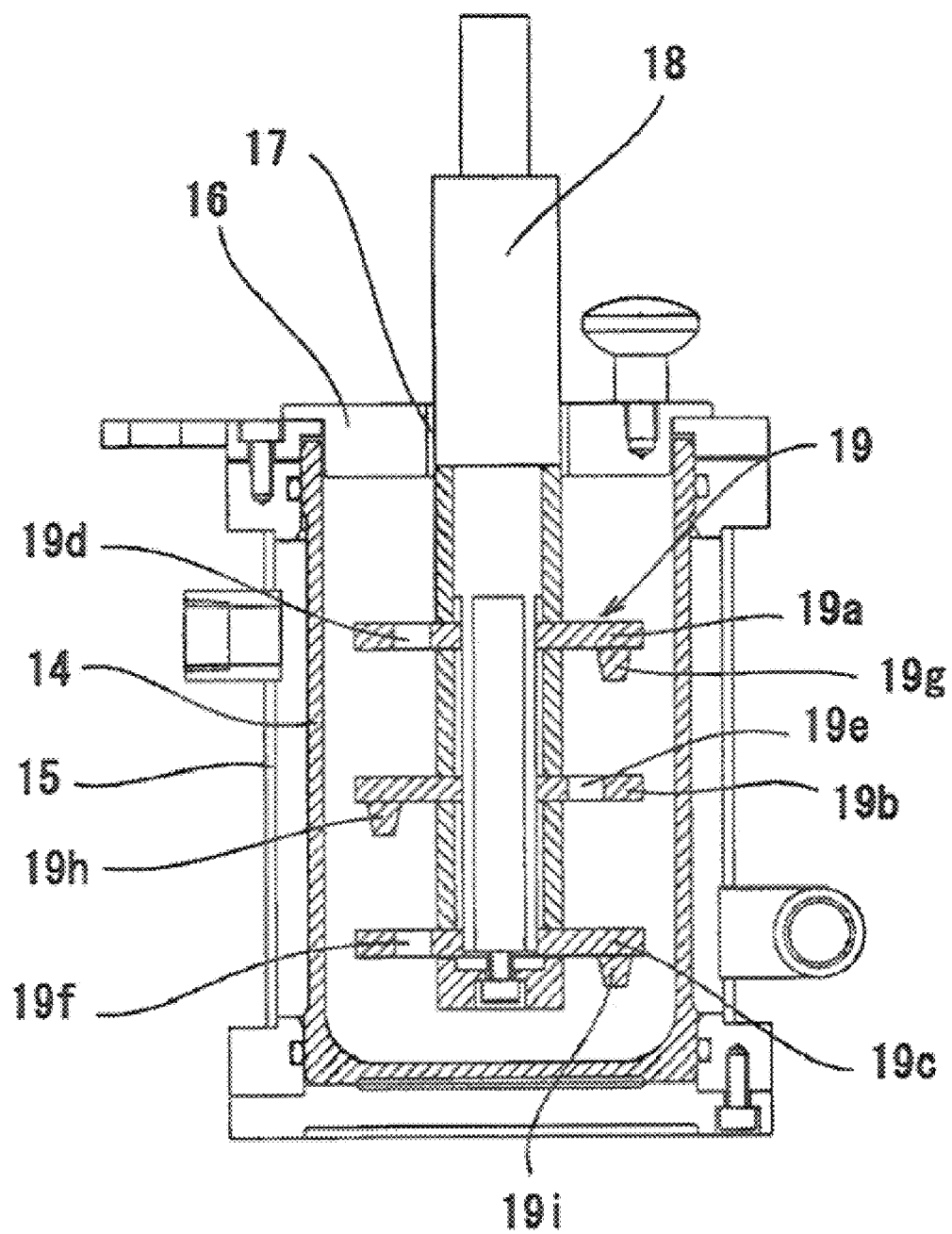

[Fig. 19]
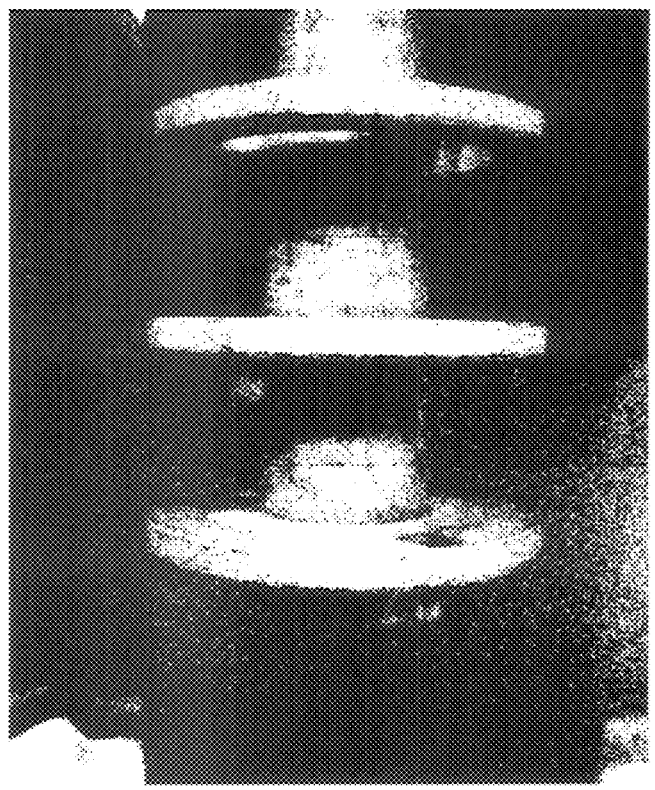
[Fig. 20]
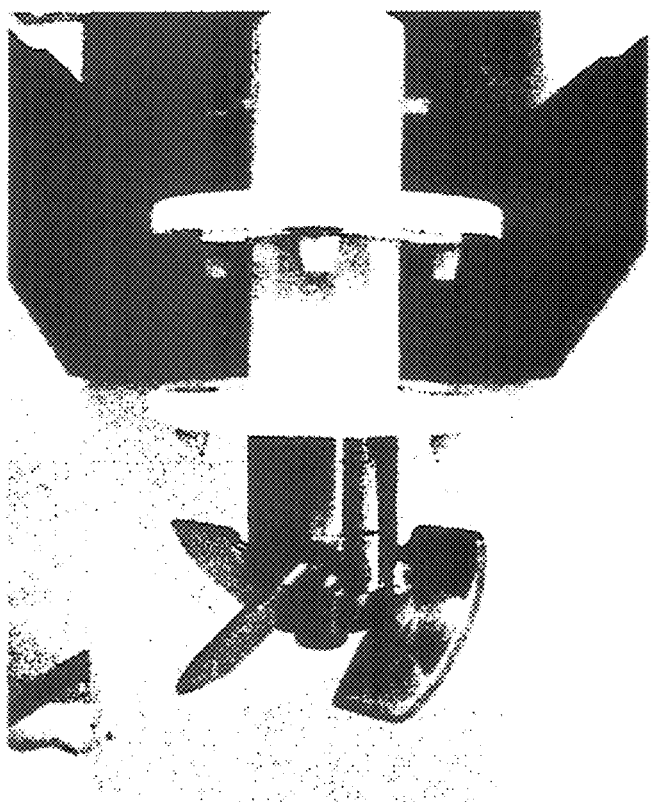

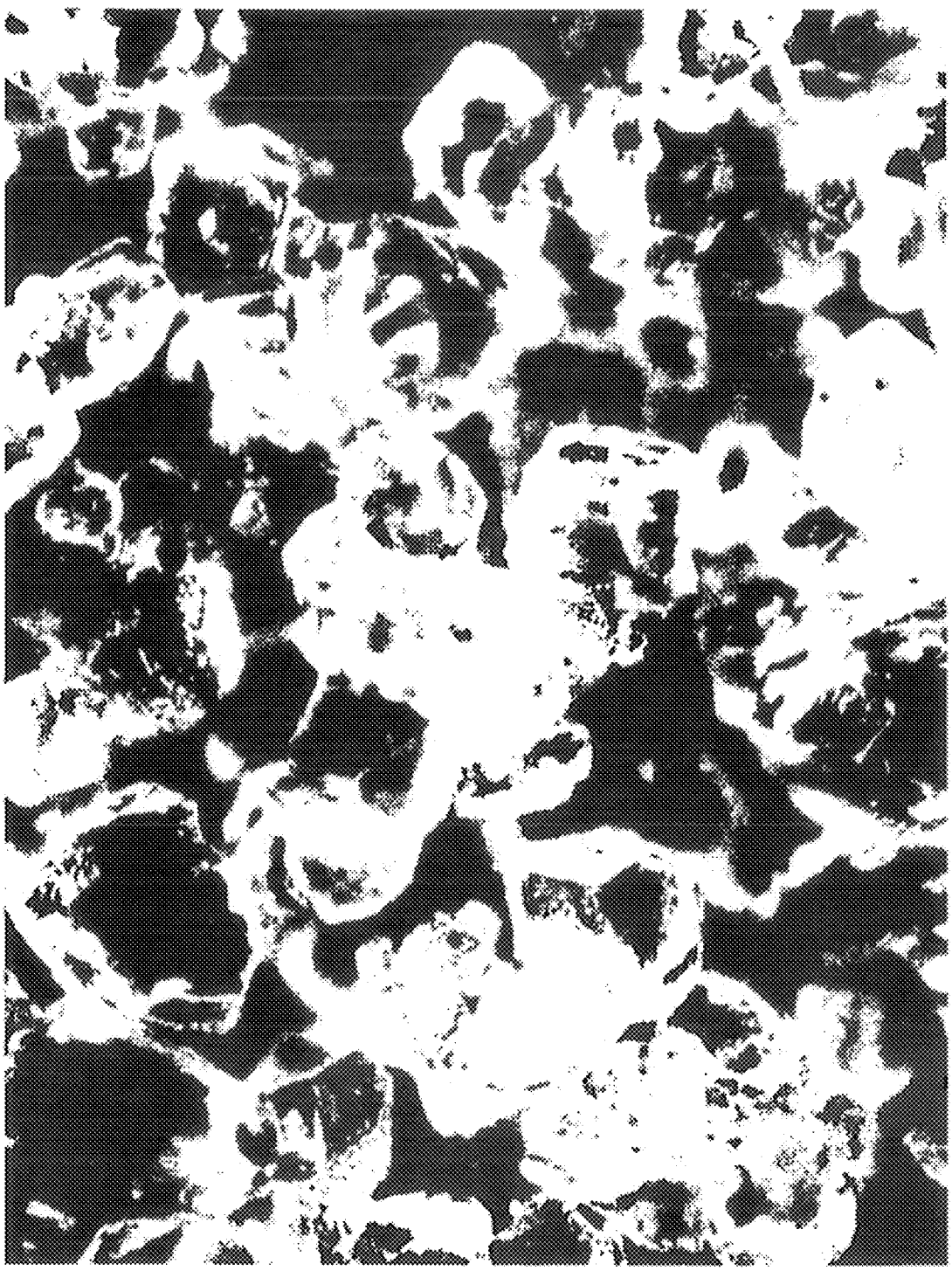
[Fig. 21]

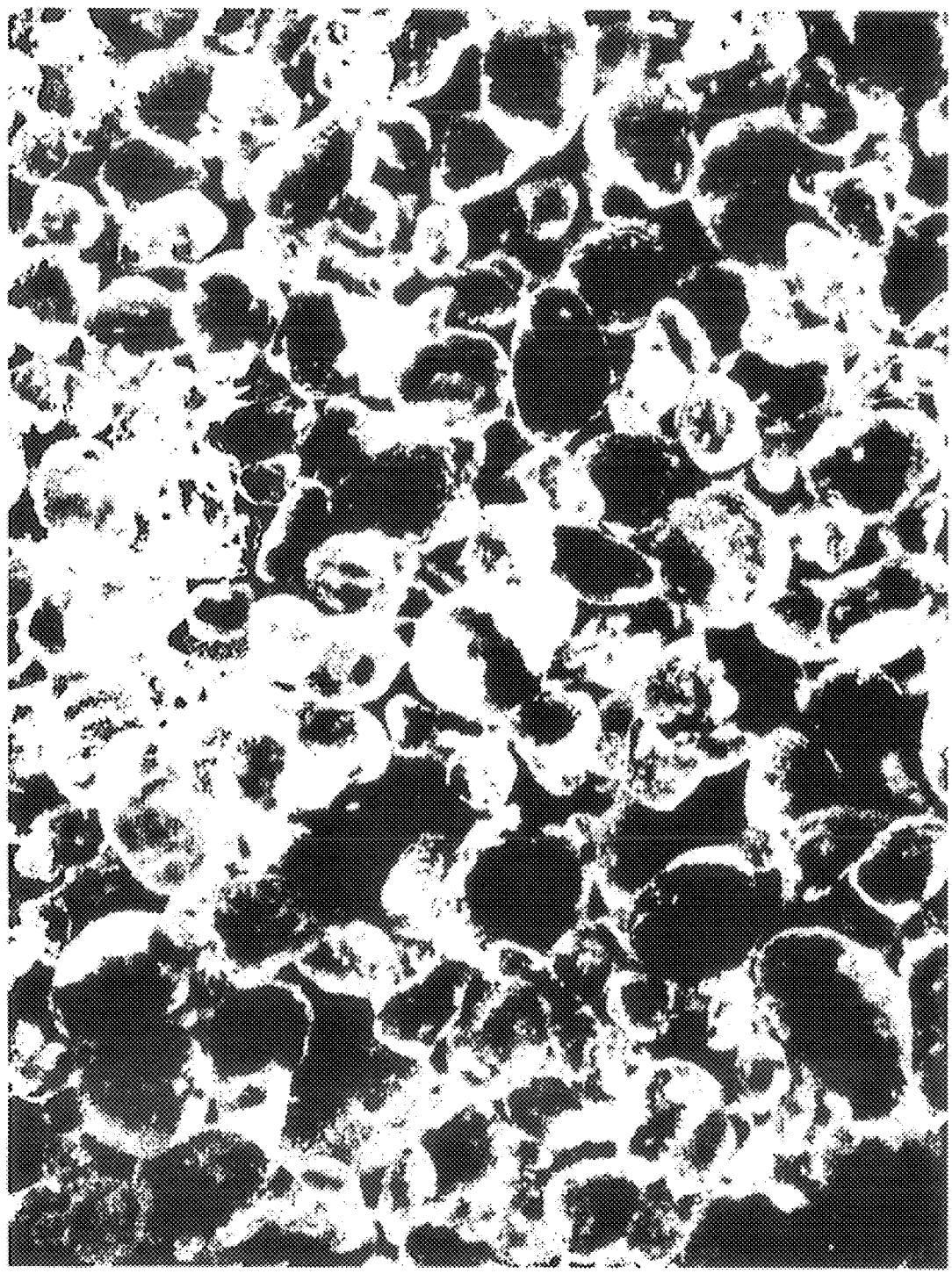
[Fig. 22]

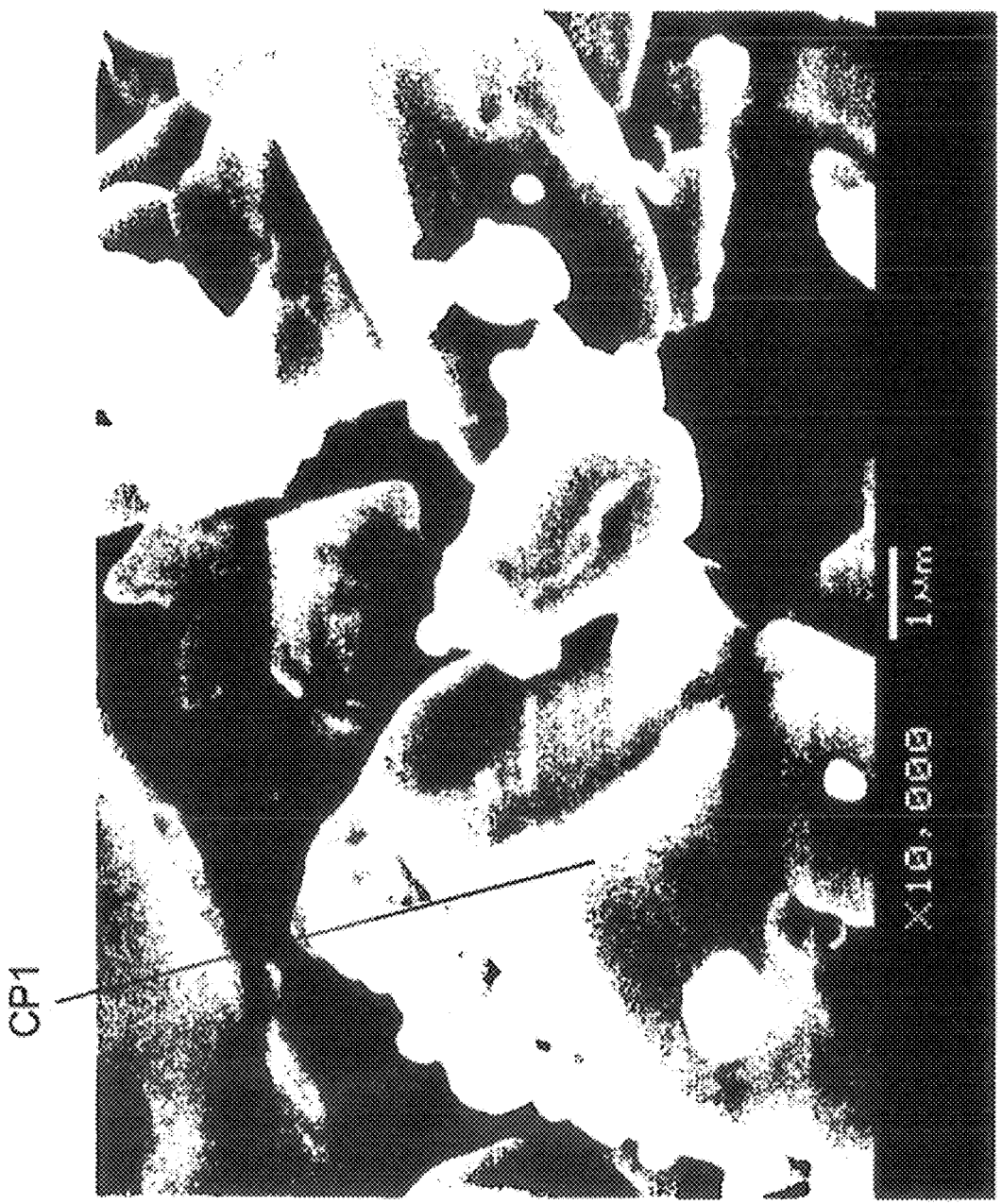
[Fig. 23]

[Fig. 24]
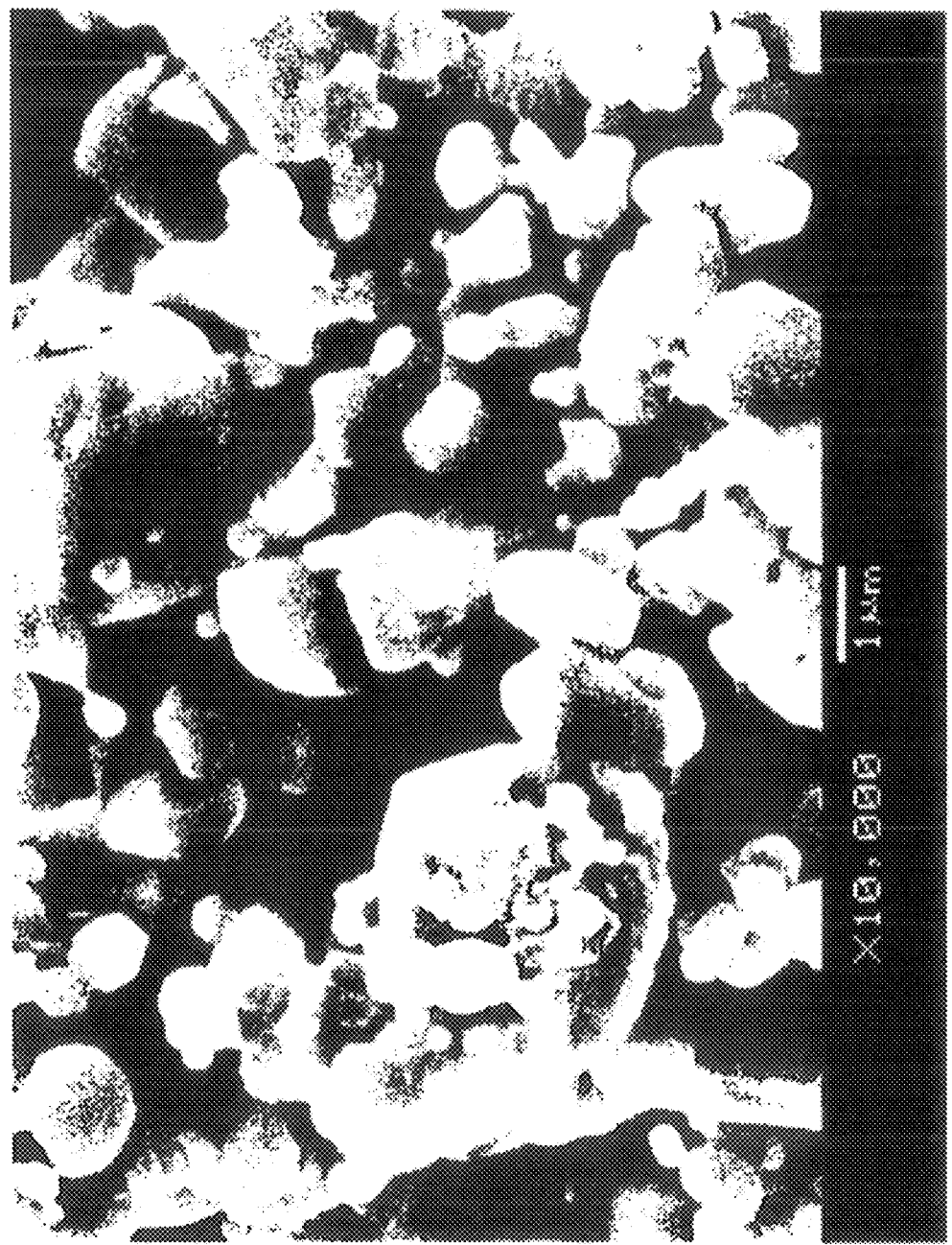

[Fig. 25]

[Fig. 26]
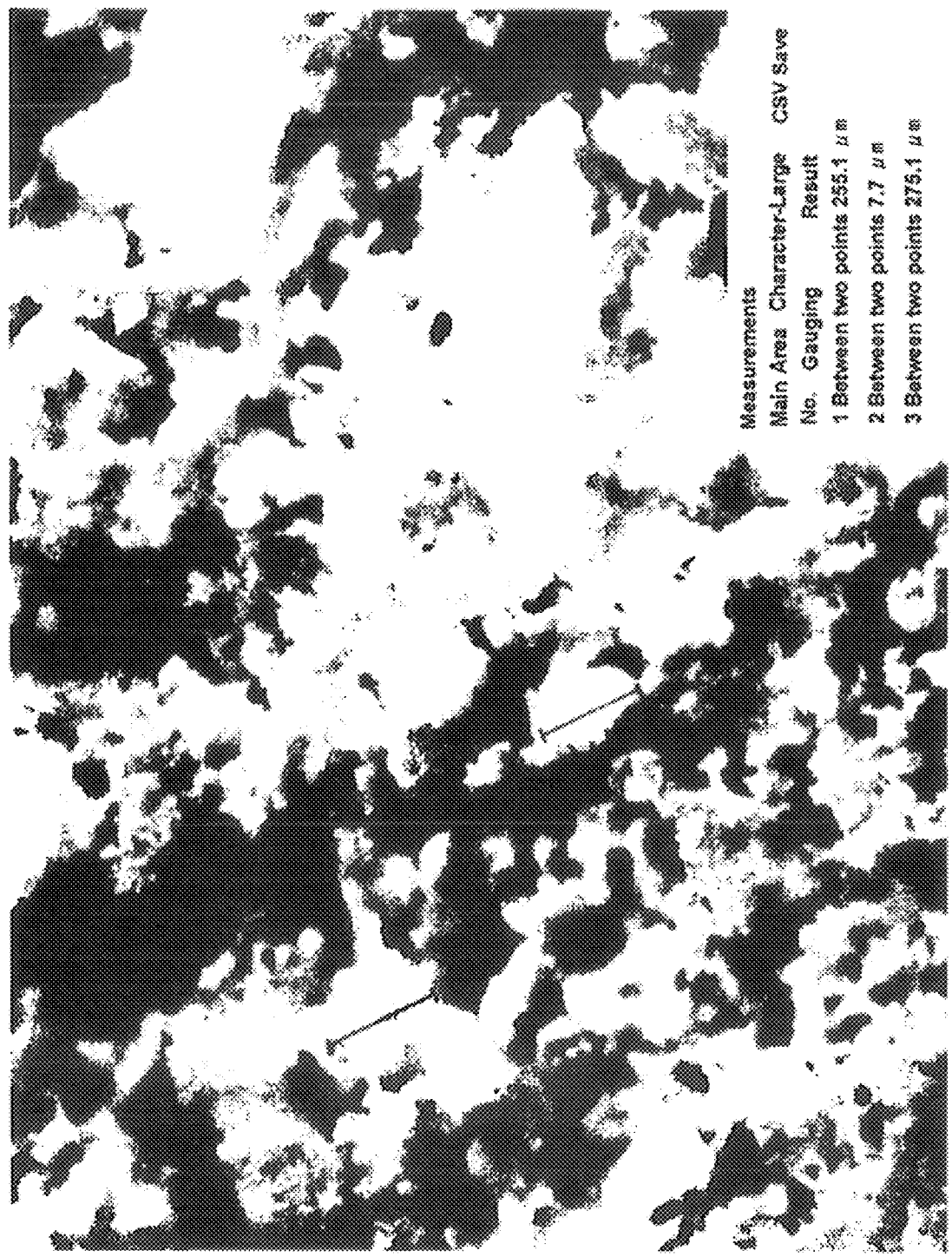

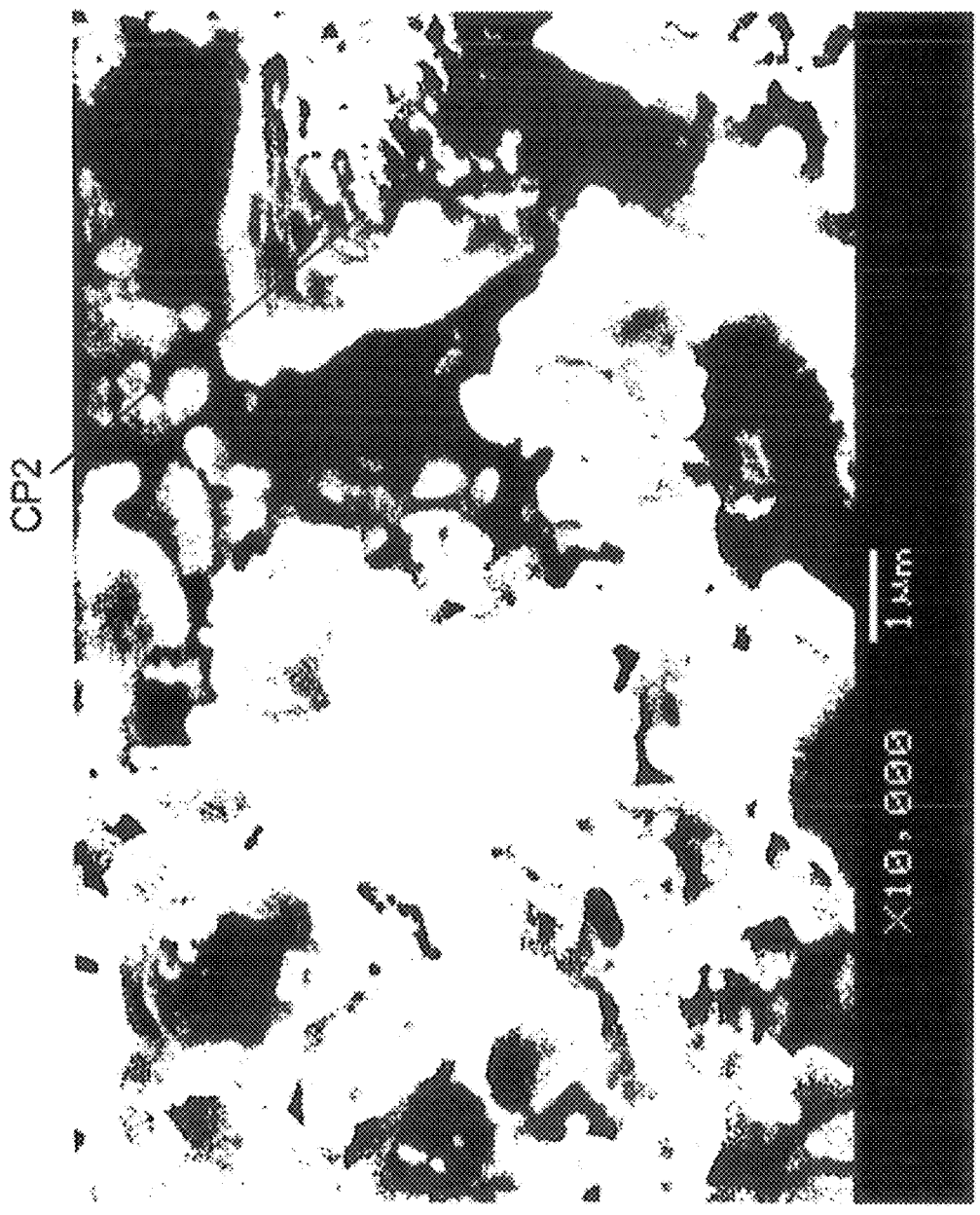
[Fig. 27]

[Fig. 28]

[Fig. 29]
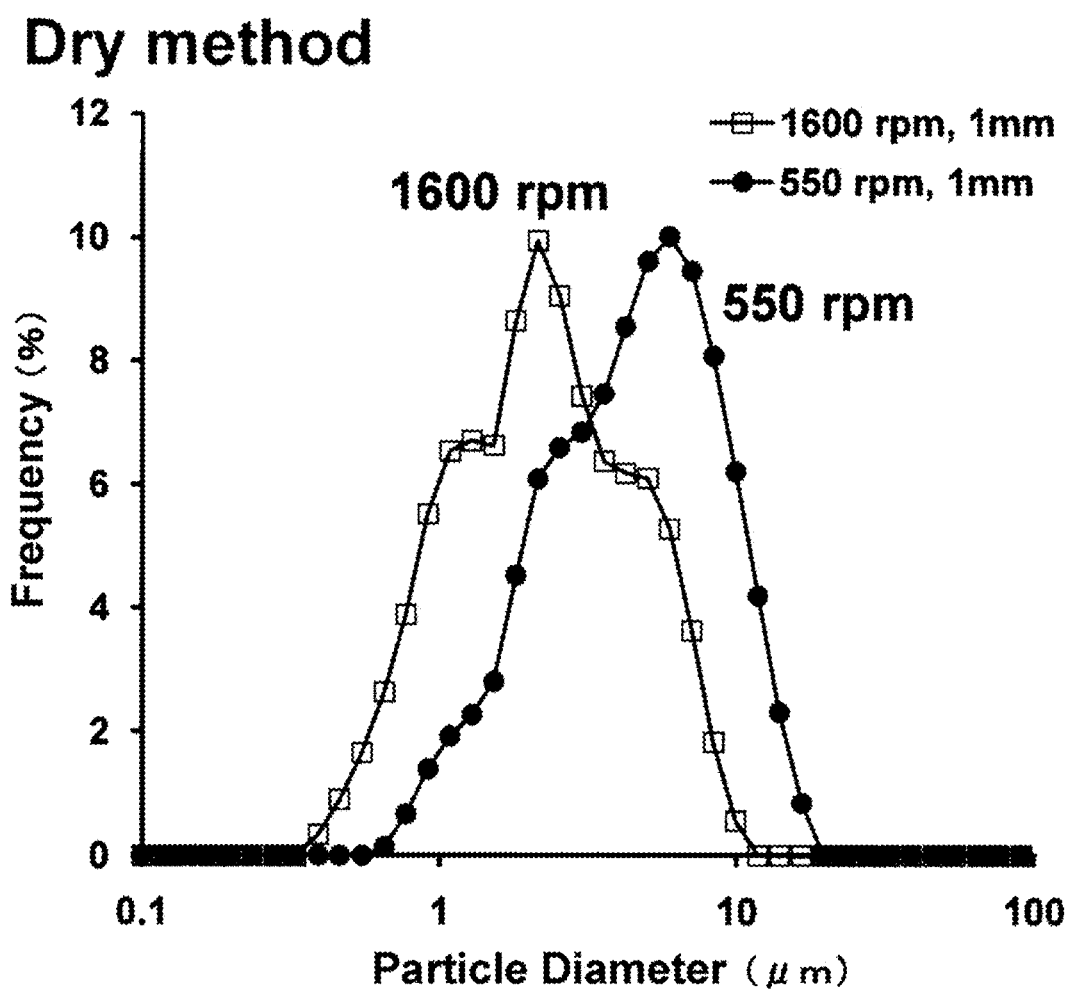

[Fig. 30]
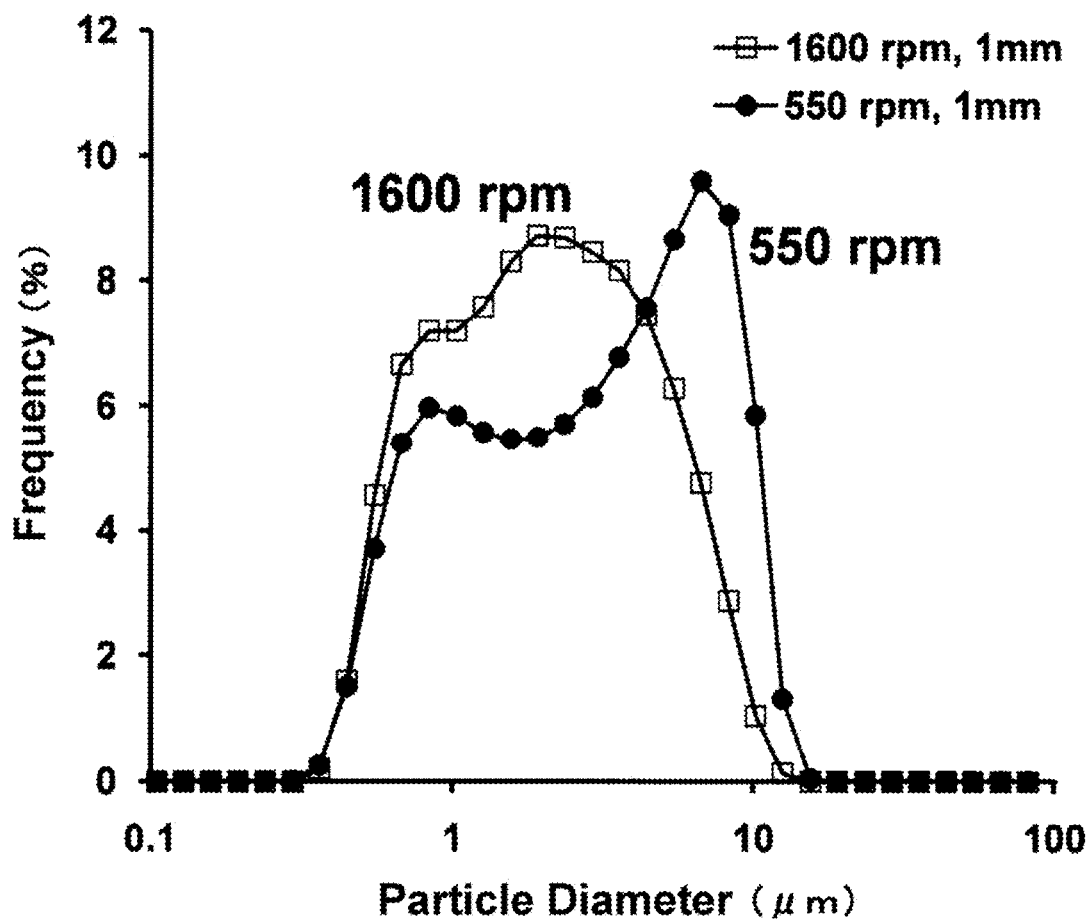

[Fig. 31]
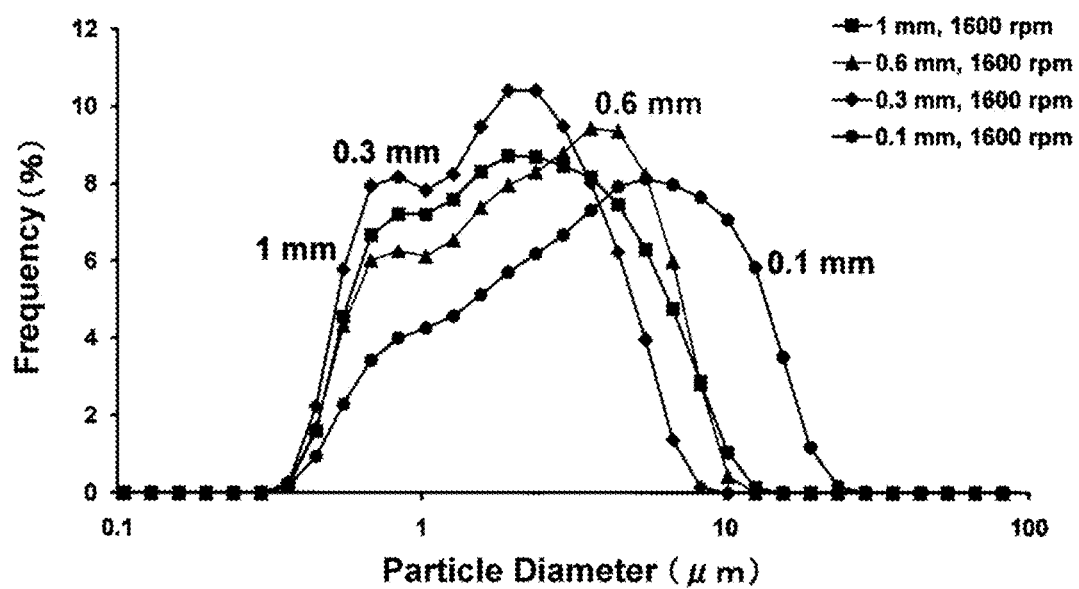

[Fig. 32]
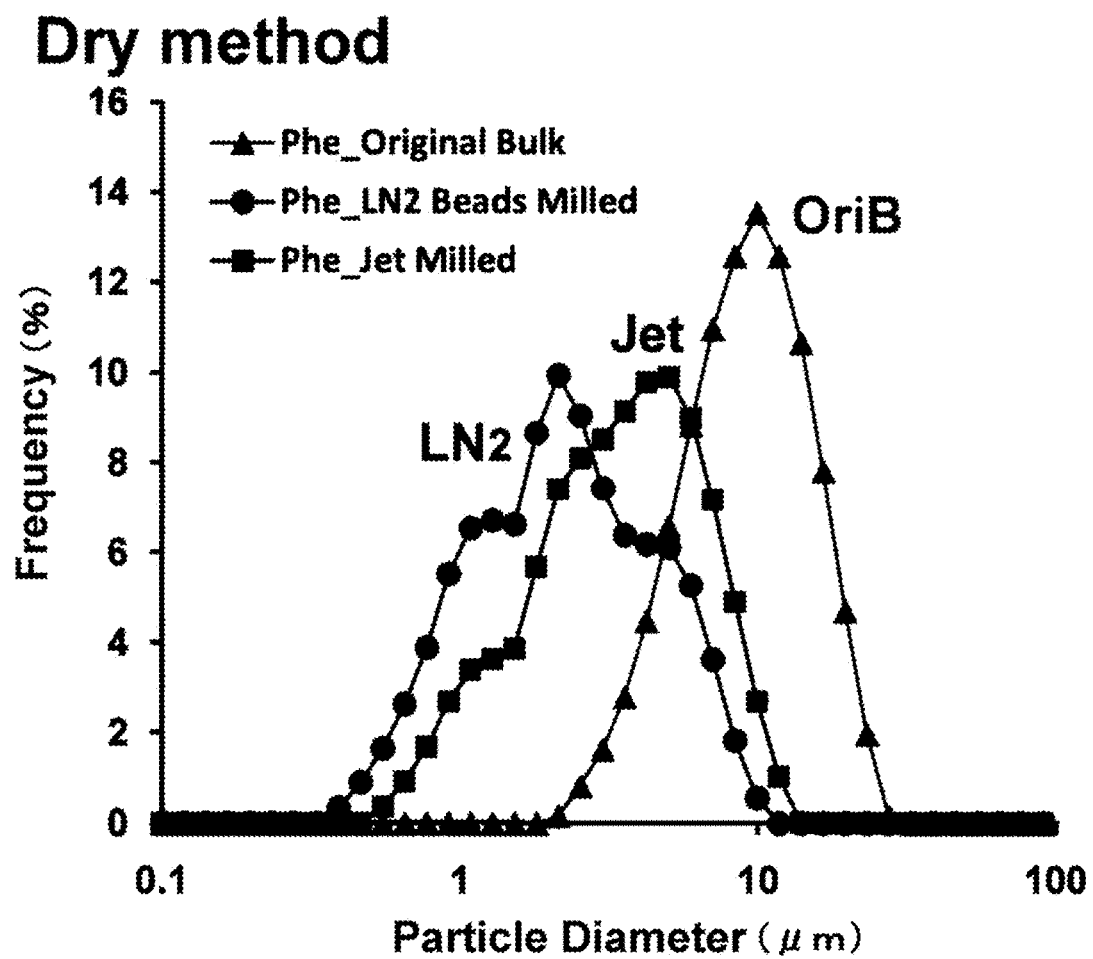

[Fig. 33]
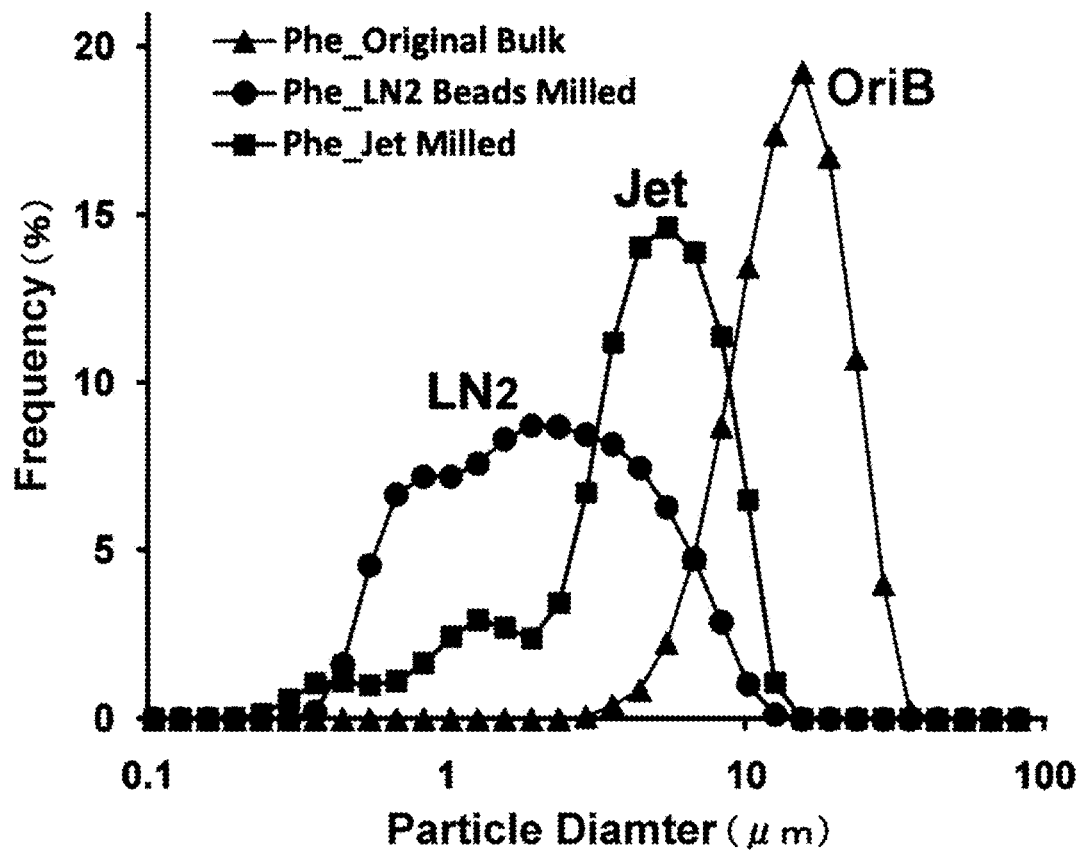

[Fig. 34]
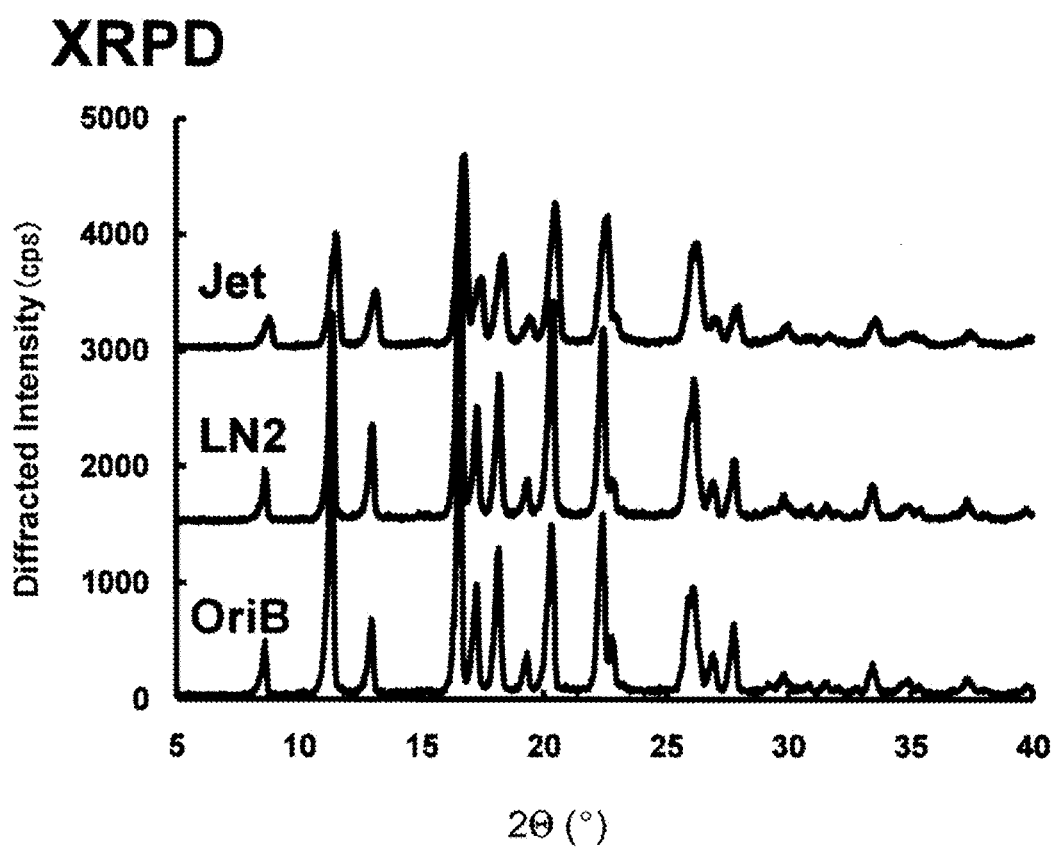

[Fig. 35]
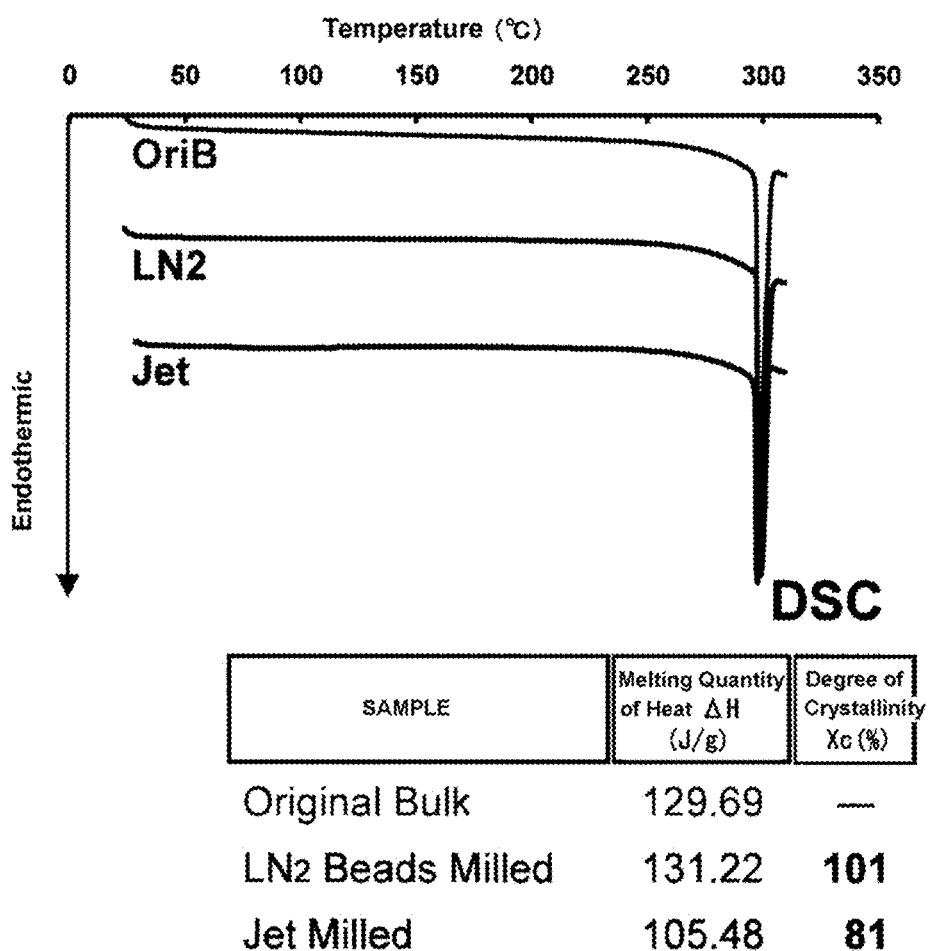

[Fig. 36]

| Additives used for Co-Grinding | D10 | D50 | D90 | nano% |
|---|---|---|---|---|
| Ungrind, for comparison | 4.0 | 8.9 | 16.9 | 0 |
| Individually ground Phenytoin, for comparison | 0.7 | 2.0 | 5.3 | 25.5 |
| HPMCAS | 0.6 | 2.0 | 7.1 | 27.9 |
| PVP | 0.9 | 3.6 | 14.7 | 14.4 |
| Eudragit L100 | 0.6 | 1.4 | 5.4 | 38.7 |
| CMC | 0.8 | 7.1 | 33.0 | 16.8 |
| MCC | 1.1 | 6.9 | 30.6 | 10.2 |
| L-HPC | 1.0 | 13.3 | 56.7 | 10.9 |
| HPMC | 1.5 | 36.2 | 82.0 | 6.0 |

[Fig. 37]

| Sampling Point | Quantity of Sample used for Measure (mg) | Result (%) |
|---|---|---|
| Site 1 | 186.05 | 0.86 |
| Site 2 | 207.69 | 0.97 |
| Site 3 | 83.69 | 1.00 |
| Site 4 | 163.77 | 0.99 |
| Site 5 | 145.86 | 1.00 |
| Site 6 | 164.78 | 1.04 |
| Site 7 | 121.32 | 1.02 |
| Site 8 | 130.41 | 0.94 |
| Site 9 | 118.69 | 1.05 |
| Site 10 | 161.38 | 1.06 |
| Average | | 0.99 |
| RSD | | 5.97 |
| Theoretical % | | 1.00 |

[Fig. 38]

| Sampling Point | Quantity of Sample used for Measure (mg) | Result (%) |
|---|---|---|
| Site 1 | 139.75 | 10.39 |
| Site 2 | 151.97 | 10.47 |
| Site 3 | 132.62 | 11.79 |
| Site 4 | 155.1 | 10.76 |
| Site 5 | 164.92 | 9.96 |
| Site 6 | 182.9 | 10.47 |
| Site 7 | 188.92 | 10.11 |
| Site 8 | 168.69 | 10.89 |
| Site 9 | 146.6 | 9.99 |
| Site 10 | 122.06 | 11.06 |
| Average | | 10.59 |
| RSD | | 5.32 |
| Theoretical % | | 10.00 |

[Fig. 39]

Before Pulverized

| | 20 | 21 | 22 | 23 | 24 | 25 | 26 | 27 | 28 | 29 | 30 | |
|---|---|---|---|---|---|---|---|---|---|---|---|---|
| 1 | 267.6 | 999.2 | 490.7 | 547.1 | 427.5 | 533.2 | 500.2 | 587.2 | 465.7 | 622.6 | 277.7 | |
| 2 | 278.8 | 881.4 | 300.0 | 460.3 | 443.8 | 556.0 | 455.4 | 564.2 | 492.9 | 341.4 | 232.0 | |
| 3 | 515.9 | 709.4 | 290.4 | 341.0 | 295.7 | 519.6 | 446.0 | 330.0 | 394.6 | 407.1 | 392.4 | |
| 4 | 360.6 | 809.2 | 521.9 | 424.8 | 230.5 | 322.6 | 404.6 | 367.9 | 548.2 | 325.5 | 515.2 | |
| 5 | 243.4 | 522.7 | 608.7 | 310.0 | 193.3 | 612.9 | 328.5 | 512.8 | 285.4 | 364.7 | 478.7 | |
| 6 | 337.4 | 615.2 | 460.9 | 312.3 | 274.4 | 475.0 | 413.5 | 276.0 | 247.1 | 793.8 | 383.3 | |
| 7 | 450.7 | 276.0 | 343.5 | 343.7 | 405.3 | 452.1 | 302.2 | 481.8 | 542.6 | 242.2 | 363.7 | |
| 8 | 496.1 | 210.2 | 366.3 | 394.5 | 156.0 | 228.1 | 321.7 | 511.3 | 385.9 | 435.1 | 211.7 | |
| 9 | 285.0 | 301.1 | 353.8 | 271.3 | 396.5 | 161.6 | 337.9 | 302.5 | 460.3 | 370.7 | 412.7 | |
| 10 | 371.3 | 295.5 | 441.7 | 408.0 | 159.1 | 588.5 | 453.2 | 307.1 | 413.1 | 423.9 | 262.2 | |
| 11 | 275.5 | 248.7 | 198.0 | 340.4 | 205.9 | 573.6 | 422.6 | 453.9 | 397.2 | 265.7 | 460.6 | |
| 12 | 255.5 | 508.8 | 491.2 | 293.5 | 269.3 | 307.8 | 203.3 | 410.7 | 460.3 | 355.1 | 349.6 | |
| 13 | 215.1 | 435.2 | 270.5 | 408.6 | 303.7 | 656.0 | 213.4 | 297.7 | 284.6 | 682.5 | 496.4 | |
| 14 | 443.2 | 491.7 | 157.3 | 392.6 | 715.7 | 304.5 | 492.5 | 336.4 | 449.2 | 277.0 | 386.1 | |
| 15 | 191.9 | 311.0 | 305.6 | 224.1 | 184.5 | 298.2 | 585.2 | 217.1 | 362.1 | 219.4 | 301.9 | |
| 16 | 198.8 | 396.9 | 357.1 | 482.4 | 236.7 | 378.5 | 230.2 | 261.8 | 394.4 | 199.9 | 381.5 | |
| 17 | 336.7 | 136.3 | 585.4 | 138.0 | 366.5 | 312.3 | 257.8 | 194.4 | 175.6 | 679.4 | 454.4 | |
| 18 | 360.1 | 441.8 | 398.4 | 174.6 | 220.1 | 542.5 | 346.7 | 398.3 | 217.1 | 439.8 | 250.4 | |
| 19 | 140.0 | 220.8 | 200.1 | 241.3 | 155.0 | 205.0 | 379.6 | 423.8 | 168.5 | 411.8 | 583.1 | |
| 20 | 210.6 | 830.6 | 230.6 | 283.7 | 364.9 | 366.5 | 298.0 | 352.2 | 451.2 | 233.6 | 285.2 | |
| Average value | 311.7 | 482.1 | 368.4 | 339.6 | 300.2 | 419.5 | 369.7 | 379.3 | 379.8 | 404.6 | 373.9 | 375.4 |
| Maximum value | 515.9 | 999.2 | 606.7 | 547.1 | 715.7 | 656.0 | 585.2 | 587.2 | 548.2 | 793.8 | 583.1 | 648.9 |
| Minimum value | 140.0 | 136.3 | 157.3 | 138.0 | 155.0 | 161.6 | 203.3 | 194.4 | 168.5 | 199.9 | 211.7 | 169.6 |
| | | | | | | | | | | | | 409.3 |

[Fig. 40]

Pulverizing Time: 120 minutes (by dry ice beads only)

| | 01 | 02 | 03 | 04 | 05 | 06 | 07 | 08 | 09 | 10 | |
|---|---|---|---|---|---|---|---|---|---|---|---|
| 1 | 429.8 | 465.4 | 315.7 | 296.7 | 461.5 | 412.4 | 464.2 | 430.2 | 461.7 | 425.9 | |
| 2 | 368.9 | 418.2 | 335.9 | 340.6 | 365.2 | 381.5 | 342.8 | 350.4 | 477.3 | 425.1 | |
| 3 | 391.0 | 465.3 | 333.2 | 296.2 | 462.9 | 317.4 | 473.5 | 326.2 | 450.9 | 355.3 | |
| 4 | 335.9 | 441.0 | 312.7 | 375.8 | 378.9 | 354.0 | 339.9 | 349.3 | 382.3 | 383.7 | |
| 5 | 341.9 | 415.7 | 419.8 | 327.3 | 403.6 | 372.6 | 295.7 | 348.0 | 381.3 | 364.3 | |
| 6 | 389.8 | 344.3 | 282.6 | 477.9 | 486.2 | 435.1 | 404.1 | 350.2 | 286.9 | 333.3 | |
| 7 | 402.4 | 246.8 | 247.6 | 258.3 | 370.5 | 317.1 | 264.7 | 261.8 | 258.5 | 268.1 | |
| 8 | 266.0 | 286.4 | 299.4 | 241.7 | 343.3 | 268.9 | 196.5 | 274.8 | 278.1 | 279.3 | |
| 9 | 274.8 | 269.8 | 221.4 | 318.0 | 370.6 | 330.9 | 331.9 | 305.5 | 290.2 | 242.5 | |
| 10 | 255.1 | 302.0 | 289.9 | 332.2 | 277.6 | 300.4 | 293.7 | 201.6 | 222.9 | 261.0 | |
| 11 | 226.3 | 291.0 | 195.9 | 226.0 | 302.2 | 267.6 | 261.9 | 250.7 | 202.0 | 252.8 | |
| 12 | 219.8 | 263.5 | 151.9 | 197.7 | 228.1 | 232.0 | 206.2 | 264.3 | 256.7 | 226.3 | |
| 13 | 273.2 | 233.2 | 267.8 | 243.1 | 319.1 | 169.1 | 90.1 | 216.9 | 204.8 | 190.3 | |
| 14 | 231.5 | 184.1 | 131.0 | 193.0 | 215.8 | 209.2 | 178.1 | 147.6 | 160.9 | 160.6 | |
| 15 | 218.2 | 170.6 | 174.8 | 169.2 | 230.4 | 232.2 | 131.2 | 201.0 | 174.7 | 215.2 | |
| 16 | 172.0 | 218.3 | 260.5 | 110.1 | 155.5 | 170.2 | 128.5 | 206.9 | 155.6 | 206.0 | |
| 17 | 176.6 | 213.2 | 166.5 | 155.2 | 191.6 | 159.6 | 265.3 | 103.7 | 100.7 | 199.6 | |
| 18 | 165.5 | 196.3 | 158.4 | 148.5 | 164.0 | 135.6 | 218.3 | 172.2 | 129.2 | 170.4 | |
| 19 | 209.1 | 146.2 | 150.8 | 129.1 | 137.3 | 95.8 | 280.1 | 180.5 | 144.8 | 126.4 | |
| 20 | 144.8 | 187.0 | 137.5 | 158.0 | 141.0 | 165.7 | 246.9 | 151.7 | 172.6 | 79.9 | |
| Average value | 274.6 | 287.9 | 242.7 | 249.7 | 300.3 | 266.4 | 270.7 | 254.7 | 259.7 | 258.3 | 266.5 |
| Maximum value | 429.8 | 465.4 | 419.8 | 477.9 | 486.2 | 435.1 | 473.5 | 430.2 | 477.3 | 425.9 | 452.1 |
| Minimum value | 144.8 | 146.2 | 131.0 | 110.1 | 137.3 | 95.8 | 90.1 | 103.7 | 100.7 | 79.9 | 114.0 |
| | | | | | | | | | | | 283.0 |

[Fig. 41]
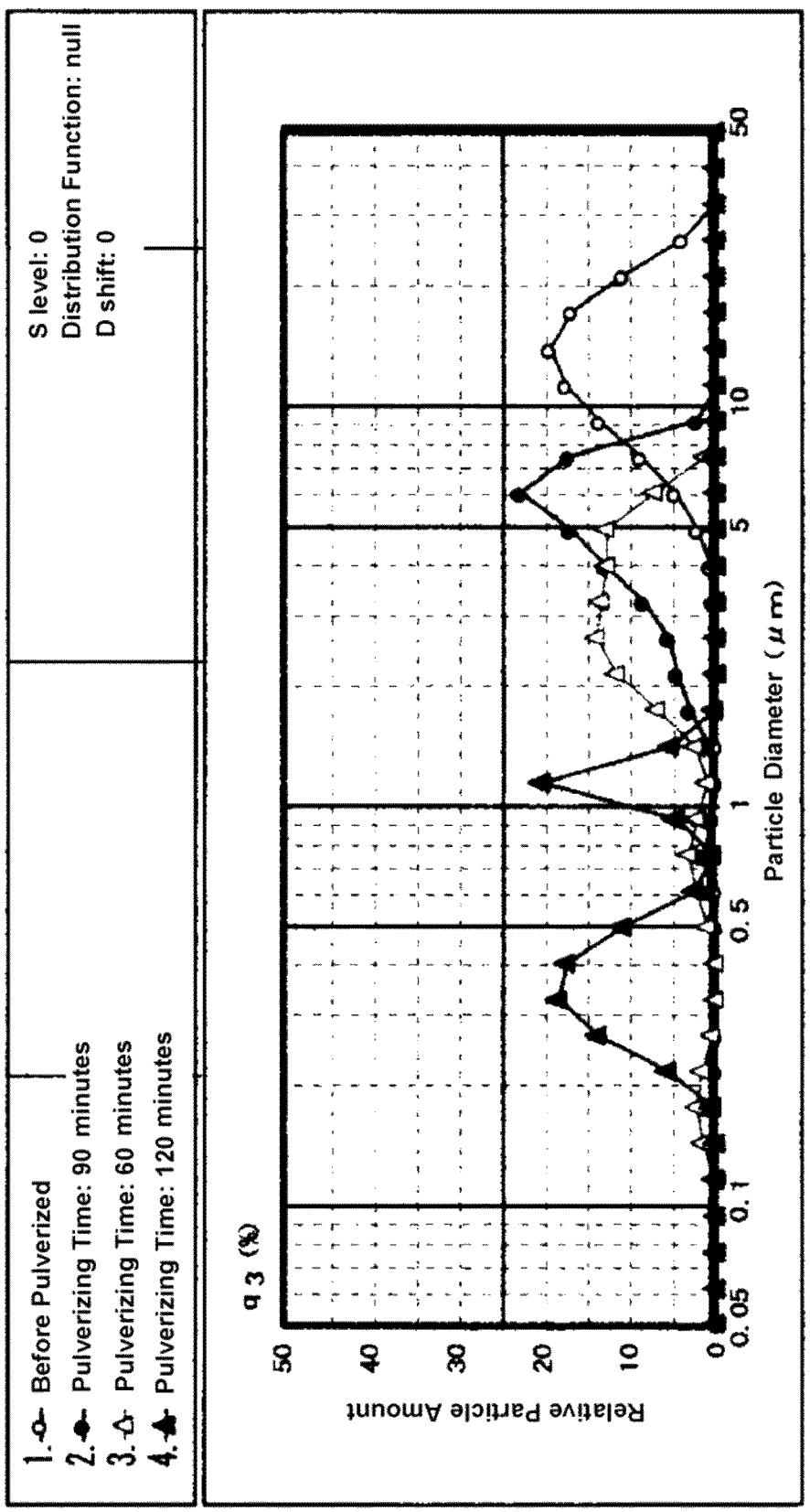

[Fig. 42]

|   | D 1 0 (μm) | D 5 0 (μm) | D 9 0 (μm) |
|---|---|---|---|
| ○ | 6.386 | 12.736 | 21.052 |
| ● | 1.981 | 4.978 | 7.576 |
| △ | 0.636 | 2.816 | 5.353 |
| ▲ | 0.256 | 0.422 | 1.221 |

○ : Phenytoin before pulverized

● : Pulverizing Time: 30 minutes

△ : Pulverizing Time: 60 minutes

▲ : Pulverizing Time: 120 minutes

[Fig. 43]
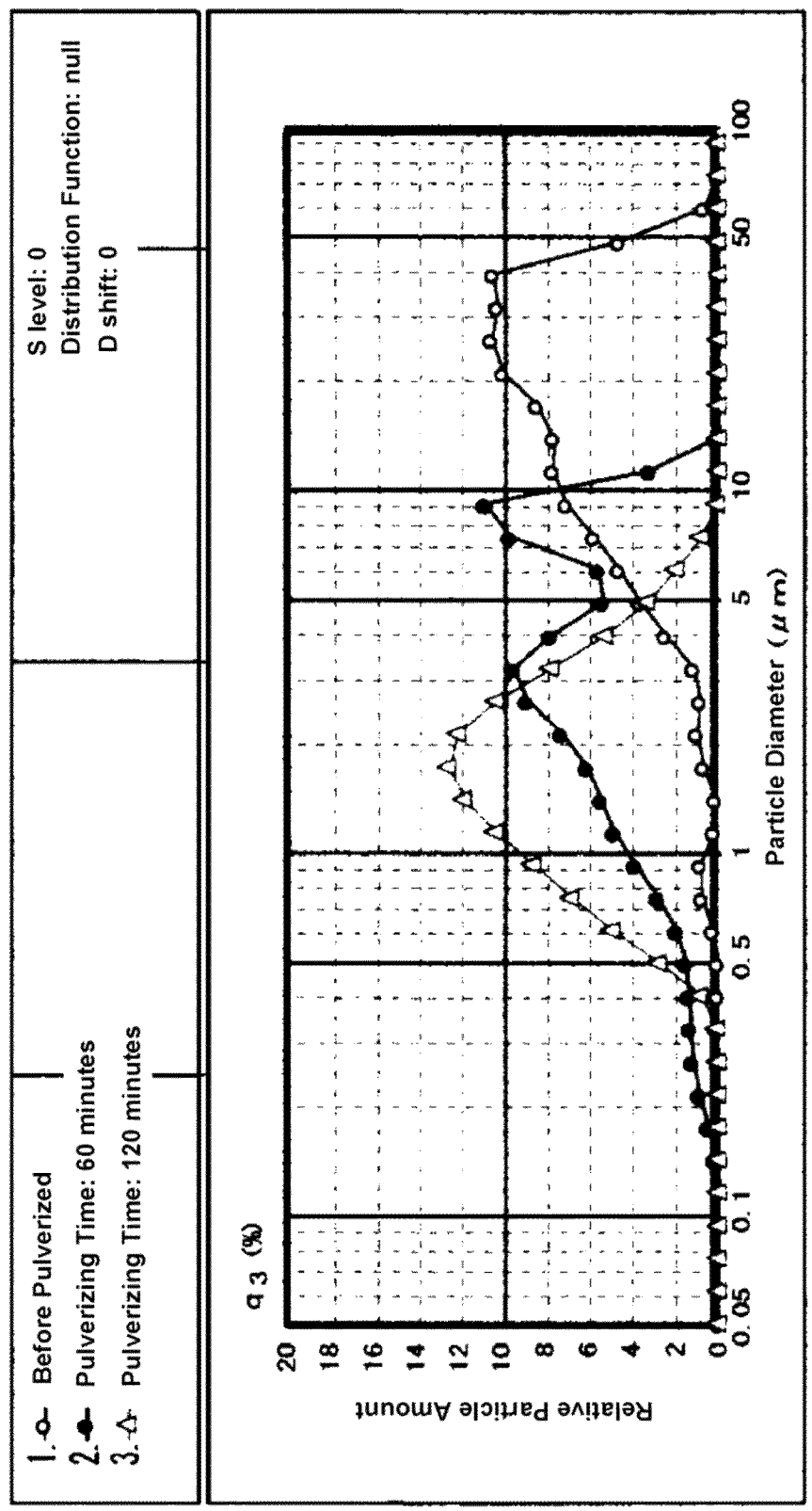

[Fig. 44]

|   | D10 (μm) | D50 (μm) | D90 (μm) |
|---|---|---|---|
| ○ | 4.762 | 17.463 | 40.041 |
| ● | 0.729 | 3.049 | 8.989 |
| △ | 0.711 | 1.675 | 3.818 |

○ : Indomethacin before pulverized

● : Pulverizing Time: 60 minutes

△ : Pulverizing Time: 120 minutes

[Fig. 45]

|   | Pulverization by dry ice | | | Pulverization by zirconia beads |
|---|---|---|---|---|
| Agitating Time (minutes) | 130 minutes | 160 minutes | 120 minutes | 15 minutes |
| Quantitative value (%) | 93.9 | 92.6 | 89.4 | 75.6 |

[Fig. 46]
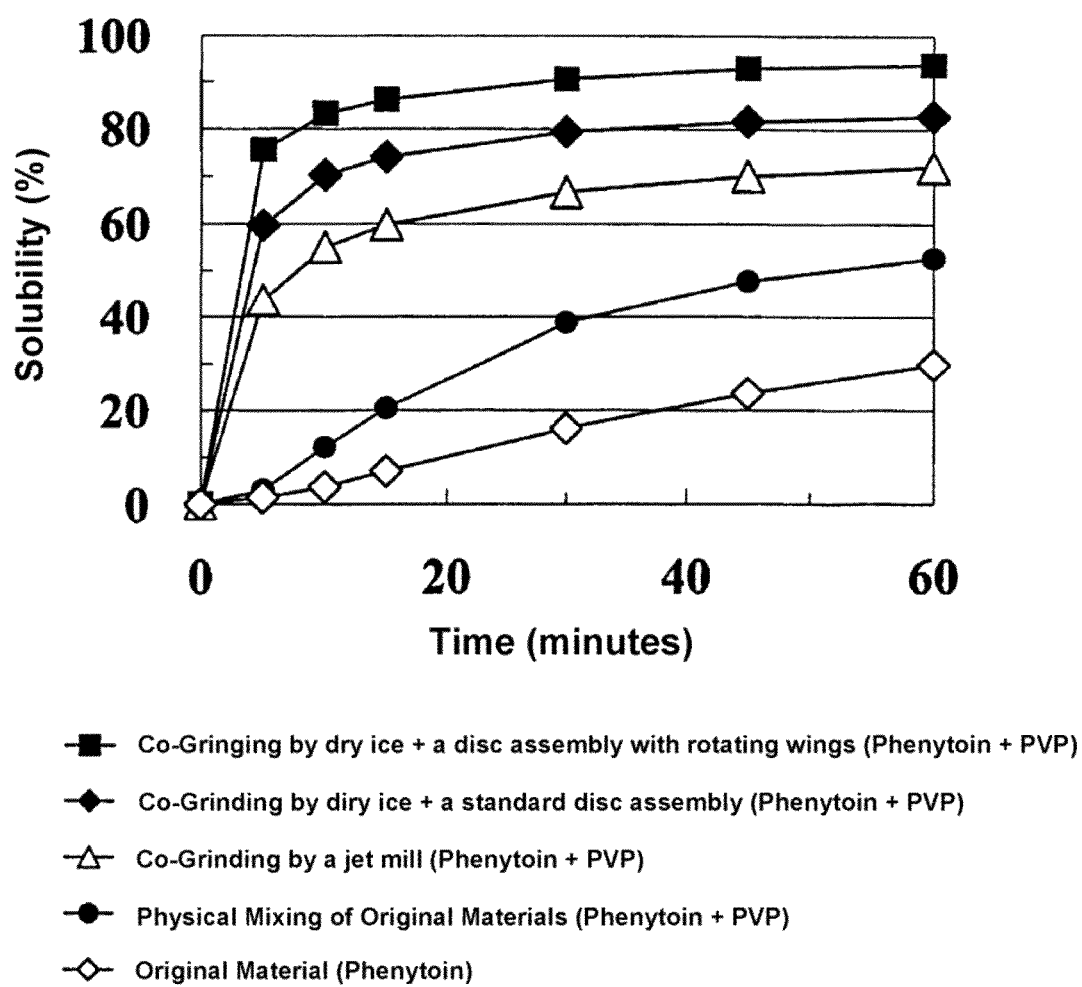

[Fig. 47]

| Co-Grinding by dry ice + a disc assembly with rotating wings (Phenytoin + PVP) | | | |
|---|---|---|---|
| Theoretical amount (%) | N=1 | N=2 | N=3 |
|  | 50 | 50 | 50 |
| 1 | 46.3 | 45.7 | 47.0 |
| 2 | 46.1 | 45.3 | 46.2 |
| 3 | 46.6 | 45.4 | 48.3 |
| 4 | 45.9 | 45.1 | 47.0 |
| 5 | 46.2 | 45.3 | 46.8 |
| 6 | 46.9 | 45.2 | 46.2 |
| 7 | 46.1 | 45.1 | 46.3 |
| 8 | 46.5 | 44.1 | 47.3 |
| 9 | 46.5 | 45.5 | 46.7 |
| 10 | 45.2 | 45.7 | 46.9 |
| Average | 46.2 | 45.2 | 46.9 |
| RSD | 1.0 | 1.0 | 1.3 |
| Quantitative value (%) | 92.5 | 90.5 | 93.7 |

METHOD FOR PRODUCING FINE POWDER AND THE FINE POWDER PRODUCED BY THE SAME

CROSS-REFERENCE TO PENDING APPLICATIONS

This application is a continuation application of U.S. patent application Ser. No. 13/509,573 filed Jul. 19, 2012, now U.S. Pat. No. 9,044,758, entitled "Method for Producing Fine Powder and the Fine Powder Produced by the Same".

BACKGROUND OF THE INVENTION

Technical Field

The present invention relates to a method for producing fine powder of raw and processed materials that are used for the products in all sorts of technical fields, such as pharmaceutical products, cosmetics, paint, copiers, solar cells, secondary batteries and recording media. The present invention further relates to the fine powder produced by the present method. The present invention especially relates to a method for producing fine powder having significantly improved dissolvability and mixing uniformity.

Background Art

The existing candidate compounds for medicines often have a low solubility. The medicines of a low solubility is not absorbed effectively from digestive organs and is increased in dosage and also varied in absorption depending upon individual differences of patients, and thereby becomes difficult in making into a pharmaceutical product in some cases. In addition, particular medicines have a very small percentage of active ingredients in the medicines. In order to expect medical effects from medicines, therefore, it is important to secure the content uniformity of active ingredients in a pharmaceutical preparation.

The fine or impalpable powder has been produced by pulverizing various forms of raw materials such as particulate and powdery materials in smaller size and/or by dispersing aggregated particles in the raw material. As such a method for producing the fine or impalpable powder as mentioned above, a dry pulverization method represented by a jet mill and a hammer mill, and a wet medium pulverization method using a solid medium for pulverization such as a ball mill and a sand mill and a bead mill have been used. In the wet medium pulverization method using a bead mill, a slurry including the raw materials is agitated in a vessel together with a number of beads, each of which is formed by a sphere having a diameter of a few hundred microns to a few millimeters, and the raw materials are pulverized to become a fine or impalpable powder, for example, by a collision of a number of beads moving in the slurry and by a dispersion of secondary aggregated particles. As the beads for pulverization or dispersion, for example, ceramic beads made of hard and chemically stable zirconia, resin beads made of urethane or nylon that can reduce metal contamination or metal beads made of abrasion-resistant stainless steel have been used.

In general, the bead that is used by the wet medium pulverization method for the purpose of pulverization or dispersion is made of the material having a higher degree of hardness than the hardness of the raw material to be pulverized.

The beads are driven by rapidly spinning desks of a wet medium pulverizer, for example, a bead mill, so that the beads gain commensurate momentum to move in the slurry at a proper speed. As a result, the beads strike against an inner wall of the vessel or a rotating shaft of the disks, and thereby abrade the inner wall of the vessel or the rotating shaft of the disks. Therefore, the materials of the vessel and the rotating shaft might mix in the slurry and contaminate the raw material to be pulverized. In addition, the beads collide with each other and are subject to wear. Therefore, the materials of the beads might also mix in the slurry.

Japanese Patent Publication No. 03-068444 (JP03-068444A) teaches that a process of charging fine powder having the particle size of below 100 μm, for example, below 10 μm into a bath of cryogenic or cryoscopic liquid prevents the particles of the fine powder from cohering and can mix a different kind of powder particles homogeneously.

Japanese Patent Publication No. 2001-046899 (JP2001-046899A) discloses a continuous circulation type bead mill, which is adapted to prevent the abrasion of a vessel etc. of a wet type media grinding machine, comprising a plurality of stirring members disposed in a cylindrical stirring tank and arranged at predetermined intervals apart from each other, a stirring part for agitating bead-like dispersion media filled in the stirring tank and a slurry-like ground material to be injected into the stirring tank, a centrifugal separation part arranged above the stirring part to centrifuge the dispersion media from the ground material and take the ground material out of the stirring tank, and means for preventing the abrasion of an upper surface of the centrifugal separation part and an inner wall of the stirring tank.

Japanese Patent Publication No. 2002-306940 (JP2002-306940A) discloses a continuous circulation type bead mill, which is adapted to use dispersion beads having very small particle size without causing any clogging with undispersed pigment particles and any wear by the dispersion beads, wherein a flow passage is formed to extend from an annular space defined by an inner wall of a vessel and an outer peripheral surface of a rotor to a discharge port of the vessel through the inside of the rotor, a centrifuge is arranged at an intermediate position of the flow passage in the rotor, the bead mill is used for centrifugally separating the dispersion beads from dispersion-treated paste due to the centrifugal force created by the rotor of the centrifuge.

Next, in the slurry retained in the vessel (a pulverization chamber) of the wet type media grinding machine, the fine powder created by the wet type media grinding machine is mixed with the beads for pulverization or dispersion. Therefore, when pulverizing other materials by the same wet type grinding machine, it is necessary to take the slurry and the beads out of the vessel to clean the vessel and it would be necessary to make a cleaning operation of the wet type grinding machine and wash out the beads taken out of the vessel.

Japanese Patent Publication No. 2007-268403 (JP2007-268403A) discloses a bead mill adapted to facilitate the maintenance of the grinding machine by minimizing the quantity of the residue slurry in the grinding machine and taking the residue slurry and the small beads out of the grinding machine, easily, completely and in a short time.

As mentioned above, the fine powder of the ground material produced by the wet type grinding machine is mixed with the beads for pulverization or dispersion in the slurry retained in the vessel of the wet type grinding machine. Usually, the beads are separated from the slurry first and then the fine powder is separated. Since the fine powder separated from the slurry is slurry-like substance, it should be subject to a drying process for producing dry powder. If the powder heated in the drying process is reaggregated, the powder should be pulverized or dispersed again.

Japanese Patent Publication No. 2003-1129 (JP2003-001129A) discloses a method for producing fine powder comprising the steps of charging usual beads for pulverization and cryogenic liquefied inert gas in a wet type grinding machine, producing a suspension formed by dispersing the materials to be pulverized in the liquefied inert gas, and pulverizing the materials by agitating the suspension together with the beads and then evaporating the liquefied inert gas to obtain dry powder. Thereby, a conventional dry process can be eliminated when producing dried-fine powder of the material to be pulverized by the wet type grinding machine.

PRIOR ART DOCUMENT

Patent Document

Patent Document 1: JP03-068444A
Patent Document 2: JP2001-046899A
Patent Document 3: JP2002-306940A
Patent Document 4: JP2007-268403A
Patent Document 5: 2003-001129A

SUMMARY OF THE INVENTION

Problems to be Solved by the Invention

Various means of wear prevention are suggested so as to prevent an abrasion of an upper surface of a centrifuge or an abrasion of an inner wall of an agitated vessel in a wet type media grinding machine, however, these means of wear prevention cannot prevent an abrasion of bead that may be caused by a collision of beads in a process of pulverization or dispersion. Zirconia is a hard and abrasion-resistant material appropriate to bead, however, a measure of abrasion of a bead cannot be avoided even by the use of zirconia beads. When producing fine powder of a high degree of purity, for example, a medicinal bulk powder and the like, it is necessary to prevent a bead material from mixing in the fine powder so as to ensure the safety of humans.

In a conventional method of a wet type medium grind performed by the use of a wet type medium grinding machine, it is necessary to separate beads for pulverization or dispersion from a slurry by a centrifuge and the like, because when the medium grinding process is completed, the beads for pulverization or dispersion remain in the slurry where the fine powder produced from a bulk material exists. The process for separating the beads increases the number of steps for producing fine powder by the use of a wet type medium grinding method.

Furthermore, the fine powder produced by the above method adheres to a surface of the beads for pulverization or dispersion and separating the beads from the slurry brings out the fine powder adhered to the surface of the beads from the slurry together with the beads. In order to collect the fine powder adhered to the surface of the beads, a further process for recovering the fine powder is necessary, and it would be difficult to collect the fine powder from the small surface of the beads. Since the conventional method of a wet type medium grind is required for a process for separating the beads used as a medium for pulverization or dispersion, as mentioned above, and thereby is subject to reduction of the recovery rate of the fine powder, the conventional method is not necessarily appropriate to a method for pulverizing such an expensive material as a bulk material of medicine and the like.

In the conventional wet grinding method that employs grinding media, the dispersive medium is mainly water and the grinding is performed at normal temperature. Therefore, a method for pulverizing the material that is hydrolysable and is easily affected by heat is required. When using water as dispersive medium, a process for separating fine powder from slurry is necessary, and a particular drying process of the fine powder is required because the fine powder is separated as powder slurry. In addition, the powder slurry has the disadvantage that it readily forms cohesive powder when dried.

In order to enhance pulverization of the material by using solid beads for pulverization or dispersion, the pulverization has to be performed by using beads having a smaller diameter as the pulverization proceeds. In other words, it is necessary to change the beads during the pulverization process or the dispersion process of the material. This is because the beads having a smaller diameter can reduce the size of powder particle. To replace the beads for pulverization or dispersion requires a process for drawing the beads having a larger diameter from the slurry and a process for putting the beads having a smaller diameter into the slurry. As a result, the number of processes for producing fine powder is increased, and the collection rate of the produced fine powder is decreased because it is difficult to collect the fine powder adhered to the beads.

The first object of the present invention is to provide an extreme cold grinding method that employs grinding media, which can pulverize materials into a submicron-sized to nano-sized powder particle; which can pulverize low-melting materials and water-soluble substances; which can pulverize materials even more uniformly; which can pulverize materials simultaneously with retaining the crystal structure of the materials; which makes it possible to obtain dry powder without an operation of liquid-solid separation.

The second object of the present invention is to provide an extreme cold grinding method that employs grinding media, which can improve the resolvability of bulk powder of drugs and medicines significantly.

Another object of the present invention is to provide a method for producing a fine power, simultaneously with avoiding the possibility of contaminating the fine power, and to provide the fine powder produced by the method of the present invention.

Further object of the present invention is to provide a method for producing fine powder, wherein a process for separating beads for pulverization or dispersion from slurry is eliminated, and to provide fine powder produced by the method of the present invention.

Further object of the present invention is to provide a method for producing a fine power, which can achieve a high collection rate of fine powder, and to provide the fine powder produced by the method of the present invention.

Further object of the present invention is to provide a method for producing fine powder, wherein the fine powder can be dried easily and can hardly agglutinate after dried, and to provide the fine powder produced by the method of the present invention.

Further object of the present invention is to provide a method for producing fine powder, which can promote pulverization of the fine powder without exchanging the beads for pulverization or dispersion, and to provide the fine powder produced by the method of the present invention.

Further object of the present invention is to provide a method for producing fine powder inexpensively, readily and without increasing the number of processes, and to provide the fine powder produced by the method of the present invention.

Means of Solving the Problems

In the first embodiment of the present invention, the raw materials for pulverization such as bulk powder for medicines and additives, for example, dispersing agents and the like, are suspended in a liquefied inert gas, for example, liquid nitrogen and the like, and then the raw materials are subjected to a dry grinding at very low temperature by a grinding method employing grinding media and are pulverized to a submicron-sized to nano-sized powder particle.

In the second embodiment of the present invention, the raw materials for pulverization and the additives are individually or simultaneously ground by means of grinding media, for example, zirconia beads and the like, in the liquefied inert gas, for example, liquid nitrogen, and then the grinding media is removed and the liquefied inert gas is vaporized. Thereby, the raw materials can be pulverized to a submicron-sized to nano-sized powder particle and the homogeneous mixture of the raw materials for pulverization and the additives can be obtained. The grinding medium is preferably a bead of zirconia, agate, quartz, titania, tungsten carbide, silicon nitride, alumina, stainless steel, soda glass, low soda glass, less soda glass, high-density glass, and dry ice (frozen carbon dioxide, frozen nitrous oxide). The particle diameter of the bead is preferably in the range of 0.03 mm to 25.00 mm, more preferably in the range of 0.03 mm to 2.00 mm. The liquefied inert gas is preferably liquid nitrogen, liquid helium, liquid neon, liquid argon, liquid krypton, liquid xenon and the like. The additives are preferably water-soluble additives for medicines and dispersion accelerating agents for medicines, such as Hypromellose-Acetate-Succinate (HPMCAS), polyvinylpyrrolidone (PVP), Methacrylic Acid Polymer (Eudragit L100), carboxymethylcellulose (CMC), microcrystalline cellulose (MMC), low substituted hydroxy-propylcellulose (L-HPC), hydroxypropyl-cellulose (HPMC), and lactose.

In the third embodiment of the present invention, the material for pulverization and granular dry ice are dispersed in liquefied inert gas, which is used as a dispersive medium, to produce the slurry and then, the slurry is agitated by a grinding machine so that the material for pulverization is pulverized in the slurry. The pulverization of the material means pulverization and/or dispersion of the material. By using granular dry ice as substitute for the conventional beads for pulverization, it can be prevented that an inner wall of a grinding vessel and a rotating shaft of a grinding machine wear by the impingement of the conventional beads and the abrasion powder of those materials mixes in the slurry; and it is also prevented that the conventional beads hit each other and the abrasion powder of the conventional beads mixes in the slurry. The conventional bead includes a ceramic bead made of alumina, agate, zirconia, silicon nitride, titania etc., a metal bead made of steel, tungsten carbide, stainless steel etc., a glass bead made of soda glass, fused quartz etc., and a plastic bead made of urethane and so on. When using the conventional bead, the conventional bead that is harder than the material for pulverization is chosen. Since those conventional bead pulverize the material by shock compression, friction, shearing and/or shear stress and so on, the bead is destroyed and any exogenous material is generated if the bead is not harder than the material for pulverization. In contrast to the conventional bead, the granular dry ice used by the present invention does not contaminate the produced fine powder because the granular dry ice sublimes and evaporates after the pulverization of the material is completed.

The third embodiment of the present invention is further characterized by the steps of: after the material is pulverized in slurry, vaporizing the liquefied inert gas from the slurry and sublimating the granular dry ice to produce dry powder of the material. The vaporization of the liquefied inert gas and the sublimation of the granular dry ice may be carried out by leaving the slurry out at room temperature. When the material is pulverized in slurry and then the liquefied inert gas is vaporized and the dry ice is sublimated, the pulverized material having the form of fine powder remains. Therefore, the fine powder can be collected directly. In other words, the pulverized material having the form of fine powder can be absolutely prevented from discharging out of the slurry together with the liquefied inert gas and the dry ice, because a process for collecting the fine powder of the pulverized material, that is, a process for separating liquefied inert gas and dry ice from slurry, is not necessary for this embodiment of the present invention. Therefore, the collection rate of the fine powder of the pulverized material can be progressed grossly. Since the collected fine powder has low water content, therefore, it can be dried easily and it can be prevented from agglutinating after dried.

The present invention uses liquefied inert gas as a dispersive medium, wherein preferred dispersive medium is liquid nitrogen, liquid helium, liquid neon, liquid argon, liquid krypton, and liquid xenon.

Carbon dioxide and nitrous oxide can be cited as the dry ice used by the present invention, wherein preferred dry ice is solid carbon dioxide.

The dry ice used by the present invention can be prepared by crushing so-called "rigid dry ice", which is formed by molding powdery dry ice, in an appropriate manner. The average size of granular dry ice used by the present invention may be determined, for example, in the rage of 0.01 mm to 25.0 mm. The average size of the granular dry ice may be set in the range of 0.10 mm to 1.00 mm. In order to pulverize the material, the average size of the granular dry ice may be determined in the range of 0.30 mm to 1.00 mm. In order to disperse the material in slurry, the average size of granular dry ice may be determined in the range of 0.03 mm to 0.30 mm. In addition, a lump of dry ice is prepared as substitute for granular dry ice and the lump of dry ice is agitated in liquefied inert gas together with the material for pulverization by means of a grinding machine, so that the lump of dry ice is crushed to granular dry ice and simultaneously, the material is pulverized and/or dispersed by the granular dry ice to obtain fine particles having a predetermined particle size. Furthermore, the particle size of dry ice can be adjusted to a desired range of diameter by the processes of putting beads for pulverization, for example, zirconia beads and the like and a lump of or granular dry ice in liquefied inert gas, pulverizing the dry ice in a grinding machine for a predetermined period of time, and then separating the beads for pulverization. In addition, the material for pulverization can be included in a grain of dry ice.

The dry ice grain used in this embodiment can be generated by the processes of filling liquid nitrogen in a container for storing liquefied gas, putting a commercially produced dry ice, for example, dry ice for shot blasting, in the liquid nitrogen, and immersing the dry ice in the liquid nitrogen for twelve hours. In the prosecution of those processes, the liquid nitrogen and the dry ice should be mixed so that the ratio of the volume occupied by the liquid nitrogen to the volume occupied by the dry ice is 2:1. The granular dry ice is obtained by separating the liquid nitrogen from the mixture after the immersion of twelve hours. The granular dry ice can be used as dry ice beads for pulverization. When the cylindrical dry ice for shot blasting having the diameter of 3.0 mm and the length of 5.0 mm to 30.0 mm, called "Shot Dry", is immersed in liquid nitrogen according to those processes, for example, for twelve hours, granular dry ice having an average diameter of 0.5 mm to 1.5 mm is generated.

The method for producing fine powder according to the present invention is further characterized by generating the slurry of material that the material for pulverization and the granular dry ice are dispersed in the dispersive medium of liquefied inert gas, and agitating the slurry in a grinding machine so that the particle size of the granular dry ice reduces while the material for pulverization is pulverized in the slurry. As the particle size of granular dry ice gradually reduces, for example, by the abrasion of the dry ice particle, the material for pulverization is pulverized to fine particles having smaller size in a similar fashion to the conventional process for enhancing the pulverization of the material by exchanging a bead of larger size to a bead of smaller size. The method for producing fine powder according to the present invention can enhance the pulverization of the material effectively only by prolonging the operation time of a grinding machine and without exchanging the beads for pulverization or dispersion.

The method for producing fine powder according to the present invention comprises the steps of generating a suspension of pulverizing material in a dispersive medium of a liquefied inert gas, and agitating the suspension together with beads for pulverization or dispersion by a pulverizer to pulverize the material in the suspension, wherein a granular dry ice is substituted for all of the beads or a part of the beads. Since the amount of beads to be used for pulverization or dispersion can be reduced by substituting granular dry ice for all of or a part of the conventional beads for pulverization or dispersion that has been used in a pulverizer, the quantity of abrasion of beads is decreased and the degree of contamination of fine powder can be reduced. By substituting the granular dry ice for a part of the beads for pulverization or dispersion, the pulverization or dispersion by the beads and by the dry ice can be performed simultaneously. Hereinbefore, liquid nitrogen can be used as the liquefied inert gas and a bead mill can be used as the pulverizer. In addition, the granular dry ice can consist of particles of solid carbon dioxide having a particle size of 0.30 to 1.00 mm.

Effects of the Invention

Due to the cold brittleness of the substance existing at a very low temperature and due to the effect of preventing particles from aggregation by the dispersive medium that permeates to a nicety of particles, the present invention can pulverize materials to fine particles of submicron size or nano-size, which cannot be attained by the conventional methods.

According to the conventional pulverization method, amorphous transformation of bulk powder is found after the pulverization, however, according to the present method for pulverization, neither crystalline transformation of bulk powder nor crystalline descent is found before and after the pulverization. In other words, the method of the present invention can pulverize bulk powder with retaining the crystal form and crystalline of the bulk powder.

The method of the present invention can pulverize low melting point materials or easily water-solvable materials. The method of the present invention can also pulverize materials more uniformly as compared to the method for pulverizing at normal temperature. Furthermore, the liquefied inert gas such as liquid nitrogen sublimes at a normal temperature and dry powder can be obtained directly from the material subject to the pulverization process. As a result, the present invention can improve the resolvability of bulk powder of drugs and medicines and, especially, the present invention will contribute to the development of pharmaceutical preparations that improves physiological application for oral administration due to the improvement of resolvability of low-solubility bulk powder of drugs. Thereby, the present invention can drastically improve the resolvability of active constituents of medicines and also improve the resolvability and the rate of dissolution of industrial materials when the present invention is applied to industrial materials.

The method of the present invention can pulverize the material and additives into the particles of submicron size or nano size so that the solvability of the pulverized material and additives can be improved dramatically and simultaneously, a homogeneous mixture of the material and additives pulverized into submicron size or nano size can be obtained by a simple and easy operation.

The method of the present invention can manufacture fine powder at a lower price and without difficulty and by smaller number of processes. Although the materials that can be pulverized by the present invention is not limited, water-soluble materials that are difficult to be pulverized by the conventional wet medium pulverization method and pharmaceutical bulk powder that should not be contaminated by any impurities can effectively be pulverized and dispersed by the method of present invention. Recently, the number of low solubility substances to be used as raw materials of pharmaceutical products is expressly increasing. It is eagerly required to improve the dissolution behavior of those medicines of low solubility by means of pulverization. The method for producing fine powder according to the present invention is expected to facilitate controlling the degree of pulverization and consequently improve the solubility and the rate of dissolution of medicines of low solubility, because the method of the present invention can improve the degree of pulverization of medicines merely by extending the processing time for pulverization, without carrying out the conventional process for changing beads. In addition, the method for producing fine powder according to the present invention can improve the collection rate of fine powder without contaminating expensive raw materials of medicines. Since the method for producing fine powder according to the present invention uses liquefied inert gas as dispersive medium, the raw materials can be pulverized without mixing dispersing agent such as a polymeric dispersant and a surfactant into the dispersive medium. Therefore, the fine powder to be produced is not contaminated with the exotic components for improving dispersion.

Further characteristics of the present invention become apparent from the following description of preferred embodiments.

BRIEF DESCRIPTION OF THE DRAWINGS

FIG. 1 shows a schematic view of an apparatus for carrying out the extreme cold medium pulverization method according to the present invention.

FIG. 2(A)-(C) are photographs of phenytoin as a medicine of low solubility, taken by a scanning electron microscope, wherein FIG. 2(A) is an electron micrograph of raw material of phenytoin taken at 3000× magnifications, FIG. 2(B) is an electron micrograph of phenytoin, pulverized by a ultra low temperature media grinding method of the present invention, taken at 10000× magnifications, and FIG. 2(C) is an electron micrograph of phenytoin, pulverized by a dry jet mill method, taken at 10000× magnifications.

FIG. 3(A)-(C) are photographs of ibuprofen as a medicine of low solubility, taken by a scanning electron microscope, wherein FIG. 3(A) is an electron micrograph of raw material of ibuprofen taken at 1000× magnifications, FIG. 3(B) is an electron micrograph of ibuprofen, pulverized by a ultra low temperature media grinding method of the present invention, taken at 5000× magnifications, and FIG. 3(C) is an electron micrograph of ibuprofen, pulverized by a dry jet mill method, taken at 5000× magnifications.

FIG. 4(A)-(C) are photographs of salbutamol sulfate as a water-soluble medicine, taken by a scanning electron microscope, wherein FIG. 4(A) is an electron micrograph of raw material of salbutamol sulfate taken at 1000× magnifications, FIG. 4(B) is an electron micrograph of salbutamol sulfate, pulverized by a ultra low temperature media grinding method of the present invention, taken at 5000× magnifications, and FIG. 4(C) is an electron micrograph of salbutamol sulfate, pulverized by a dry jet mill method, taken at 5000× magnifications.

FIG. 5 is a diagram illustrating the dissolution behavior of pulverized mixture of phenytoin and hydroxypropylmethylcellulose acetate succinate (HPMCAS). (Example 12)

FIG. 6 is a diagram showing the dissolution behavior of pulverized phenytoin. (Reference example 1)

FIG. 7 is a diagram showing the dissolution behavior of a mixture of phenytoin and commercially available additives (lactose and L-HPC). (Reference example 2)

FIG. 8 is a diagram showing the dissolution behavior of a pulverized mixture of phenytoin and polyvinylpyrrolidone (PVP). (Example 13)

FIG. 9 is a diagram showing the dissolution behavior of a pulverized mixture of phenytoin and Methacrylic Acid Polymer (Eudragit L100). (Example 14)

FIG. 10 is a diagram showing the dissolution behavior of a pulverized mixture of phenytoin and Carboxymethyl cellulose (CMC). (Example 15)

FIG. 11 is a diagram showing the dissolution behavior of a pulverized mixture of phenytoin and microcrystalline cellulose (MCC). (Example 16)

FIG. 12 is a diagram showing the dissolution behavior of a pulverized mixture of phenytoin and low substituted hydroxy-propylcellulose (L-HPC). (Example 17)

FIG. 13 is a diagram showing the dissolution behavior of a pulverized mixture of phenytoin and hydroxy-propylcellulose (HPMC). (Example 18)

FIG. 14 is a diagram showing the solubility of pulverized materials and additives. (Example 18)

FIG. 15 is a diagram showing the dissolution behavior of the sample, which chemical compound (phenytoin) and additive (PVP) are concurrently pulverized, and the dissolution behavior of the sample, which chemical compound (phenytoin) and additive (PVP) are individually pulverized, respectively and mixed with liquid nitrogen before dried. (Example 20)

FIG. 16 is a diagram showing the dissolution behavior of the sample, which chemical compound (phenytoin) is individually pulverized and mixed with untreated additive (PVP). (Example 21)

FIG. 17 is an overall view of a wet media-agitating mill that is available for the method for producing fine powder according to the present invention; wherein FIG. 17(A) illustrates a front view of the mill and FIG. 17(B) illustrates a left side view of the mill.

FIG. 18 illustrates a vertical section view of a pulverization vessel of the wet media-agitating mill.

FIG. 19 is a photograph of the standard type discs to be installed in the wet media-agitating mill in FIGS. 17 and 18.

FIG. 20 is a photograph of the discs with rotating blades to be installed in the wet media-agitating mill in FIGS. 17 and 18.

FIG. 21 is a photograph of the particles of dry ice taken by a digital type optical microscope at 100× magnifications before pulverization.

FIG. 22 is a photograph of the pulverized particles of dry ice taken by a digital type optical microscope at 100× magnifications.

FIG. 23 is a photograph of the phenytoin pulverized by the method for producing fine powder according to the present invention for 30 minutes and then taken by an electron microscope at 10000× magnifications.

FIG. 24 is a photograph of the phenytoin pulverized by the method for producing fine powder according to the present invention for 60 minutes and then taken by an electron microscope at 10000× magnifications.

FIG. 25 a photograph of the phenytoin pulverized by the method for producing fine powder according to the present invention for 120 minutes and then taken by an electron microscope at 10000× magnifications.

FIG. 26 is a photograph of the mixture of phenytoin and dry ice particles, taken by a digital type optical microscope at 100× magnifications, after pulverizing phenytoin by means of dry ice particles according to the method for producing fine powder of the present invention for 30 minutes and then vaporizing liquid nitrogen.

FIG. 27 is a photograph of indomethacin pulverized according to the method for producing fine powder of the present invention for 60 minutes and taken by an electron microscope at 10000× magnifications.

FIG. 28 is a photograph of indomethacin pulverized according to the method for producing fine powder of the present invention for 120 minutes and taken by an electron microscope at 1000× magnifications.

FIG. 29 is a graph or chart showing a dry method particle size distribution;

FIG. 30 is a graph or chart showing a wet method particle size distribution;

FIG. 31 is a graph or chart showing a wet method particle size distribution;

FIG. 32 is a graph or chart showing a dry method particle size distribution;

FIG. 33 is a graph or chart showing a wet method particle size distribution;

FIG. 34 is a graph or chart showing the results of powder x-ray diffractometry;

FIG. 35 is a graph or chart representing differential scanning calory;

FIG. 36 is a graph or chart showing additives and a rate of pulverized particles having a diameter of 1 μm and below;

FIG. 37 is a chart showing mixing rates;

FIG. 38 is a chart showing mixing rates of the mixture;

FIG. 39 is a chart showing particle sizes of dry ice before pulverization;

FIG. 40 is a chart showing particle sizes of dry ice after agitation in liquid nitrogen;

FIG. 41 is a graph or chart showing measured distribution of particle size;

FIG. 42 is a graph or chart showing average particle diameters;

FIG. 43 is a graph or chart showing measured distribution of particle size of indomethacin;

FIG. 44 is a graph or chart showing average particle diameter of indomethacin;

FIG. 45 is a chart of the quantitative value (%) from pulverization;

FIG. 46 is a graph or chart illustrating solubility over time; and

FIG. 47 is a chart showing results of grinding by dry ice and a disc assembly.

EMBODIMENTS OF THE INVENTION

Figure 2A:
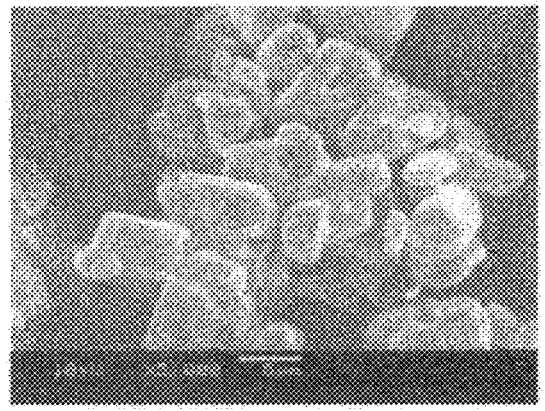

The material or substance that can be pulverized by the present invention is not limited to extraordinary materials or substances. However, the present invention is especially available for pulverization of raw material of low dissoluble medicines such as Phenytoin and Ibuprofen.

The additives or addition agents that is available for the present invention may be additives that are usually used as additives of medicines, such as hydroxypropylmethylcellulose acetate succinate (HPMCAS), polyvinylpyrrolidone (PVP), Methacrylic Acid Polymer (Eudragit L100), Carboxymethyl cellulose (CMC), microcrystalline cellulose (MCC), low substituted hydroxy-propylcellulose (L-HPC) hydroxy-propylcellulose (HPMC) and lactose. The additives should be selected as appropriate according to the kind of material concurrently pulverized with the additives.

As to beads that would be available for the present invention, the beads made of the materials such as zirconia, agate, quarts, titania, tungsten carbide, silicon nitride, alumina, stainless steel, soda glass, low soda glass, soda less glass, high density glass and dry ice (carbon dioxide, nitrous oxide) can be quoted. The adequate diameter of a particle of a bead is considered to be within the range from 0.03 to 25 mm, preferably within the range from 0.03 to 2 mm. The material and size of a bead should be determined depending on the properties of the material and additive to be pulverized and the targeted size of particles etc.

The method of the present invention is performed under the extreme cold condition generated by liquefied inert gas such as liquid nitrogen, liquid helium, liquid neon, liquid argon, liquid krypton and liquid xenon. Among these liquefied gases, liquid nitrogen is most preferable for the present invention.

According to the pulverizing method of the present invention, pulverized and homogeneously mixed particles can be obtained by the steps of: pulverizing the material and additives in liquefied inert gas at a ultra low temperature with use of medium of bead, and removing the beads by the means commonly used in the technical field and evaporating or spontaneously evaporating the liquefied inert gas.

As a result of concurrently pulverizing the material and additives in liquefied inert gas at ultra low temperature with use of medium of bead, the material and additives can be simultaneously pulverized into submicron-sized particles or nano-sized particles whereby pulverized materials having improved resolvability can be produced. After the simultaneous pulverization of the material and additives, the medium of pulverization is removed by commonly used means and the liquefied inert gas is evaporated or spontaneously evaporated, whereby the pulverized and homogeneously mixed particles having improved resolvability can be obtained.

On the other hand, the pulverized and homogeneously mixed particles can be obtained by the steps of: individually pulverizing the material and the additives in liquefied inert gas at ultra low temperature with use of medium of bead, removing the medium of bead by the means commonly used in the field of technology, mixing the slurry containing the pulverized material with the slurry containing the pulverized additives, and evaporating or spontaneously evaporating the liquid nitrogen.

Since the method of the present invention can be operated with use of a bead mill etc. in accordance with the manner of operation commonly used in the technical field, the manner of operation is not described in detail in the specification of this application.

BRIEF SUMMARY OF EXAMPLE 1-4

Materials

Phenytoin and Ibuprofen (low melting point: 76° C.) were used as very insoluble medical agent. Salbutamol sulfate was used as water-soluble medical agent. Zirconia bead (a small sphere, spherule) (YTZ ball by NIKKATO CORPORATION) having the particle diameter of 0.1 mmØ, 0.3 mmØ, 0.6 mmØ, and 1.0 mmØ was used as a grinding medium.

Pulverizing Apparatus

The ultra low temperature medium pulverizing apparatus (LN2 Bead Mill) that is schematically illustrated in FIG. 1 was used. This apparatus is a batch bead pulverizer (Ready Mill RMB-4, AIMEX CO., LTD.) that has been modified as a device for pulverizing in liquid nitrogen. The apparatus comprises a vessel 1 and rotating discs 3, all of which are made of zirconia.

Basic Physicality of Liquid Nitrogen (LN2)

Low responsiveness and avirulent: nonreactive to contactant
Boiling point: −196° C.
Low lytic potential: Not dissolving almost all solid materials
Surface tension value: 10.5 mN/m (which is approximately seventh part of the surface tension value of water and LN2 has a high wettability to powder.)
Degree of viscosity: $0.15 \times 10^{-2}$ poise (which is approximately seventh part of the viscosity of water and LN2 is easy to penetrate through fine pores.)
Latent heat of vaporization: 47.7 Kcal/Kg (which is eleventh part of the latent heat of vaporization of water and LN2 rapidly evaporate at normal temperature and at normal pressures.)

The Method of Ultra Low Temperature Medium Grinding

In an ultra low temperature medium grinding apparatus (LN2 bead mill) illustrated in FIG. 1, the bulk volume of 180 mL (the weight of 658 g) of a zirconia bead (a spherule) 4 having a diameter of 0.1 mmø, 0.3 mmø, 0.6 mmø or 1.0 mmø was put into a vessel 1 having a volume of 400 mL and then the bulk volume of 50 mL (the weight of 15 g to 20 g) of medical substance was fed into the vessel 1. Next, liquid nitrogen 5 was fed into the vessel 1 to occupy the volume of 90% in the vessel 1. And, by rotating a rotating shaft 2 at a predetermined velocity, a medium grind (bead milling) was performed. The rotating shaft 2 was continuously rotated for 30 minutes while liquid nitrogen 5 was supplied to the vessel 1 as needed to make up for the loss caused by vaporization of liquid nitrogen 5. After the pulverization, the beads were sieved from the slurry by use of a sieve having apertures corresponding the size of bead. The sieved slurry was left at a room temperature and under atmospheric pressure in order to volatilize liquid nitrogen 5 from the slurry. Thereby, the dry powder of pulverized particles was obtained.

The Dry Method for Pulverization by Use of a Jet Mill
Bulk powder 20 g were pulverized under air pressure of 0.7 MPa by a jet mill (A-O jet mill, SEISHIN ENTERPRISE CO., LTD.) and the results of the jet milling were compared with the results of the ultra low temperature medium grinding.

Evaluation Method of Pulverized Particles
(1) Observation by a Scanning Electron Microscope (SEM)
The exterior appearance of pulverized particles on which platinum is deposited was observed by a scanning electron microscope (JSM-6060, JEOL LTD.).
(2) Particle Size Distribution
The pulverized particles were dispersed by compressed air (0.4 MPa) and then, the dry particle size distribution was measured by a laser diffraction apparatus for measuring particle size distribution (LMS-30, SEISHIN ENTERPRISE CO., LTD.). On the other hand, the pulverized particles were dispersed in purified water by ultrasonic dispersion (30 seconds) and then, the wet particle size distribution was measured by a laser diffraction apparatus for measuring particle size distribution (SALD-2100, SHIMADZU CORPORATION).
(3) Crystalline Properties
The crystalline states of the bulk powder and the pulverized particles were measured by a X-ray powder diffraction apparatus (RAD-2VC, Rigaku Corporation) and a differential scanning calorimeters (DSC-60, SHIMADZU CORPORATION). In addition, a quantity of heat for melting (J/g) that was calculated on the basis of a peak area of melting point on the DCS curve was used as an index of the degree of crystallization.

EXAMPLE 1

Figure 2B:
Figure 2C:

FIG. 2 shows electron micrographs (SEM) of the original bulk of phenytoin and the pulverized particles of phenytoin. Comparing FIG. 2(B) and FIG. 2(C), it was found that the particles pulverized by the LN2 bead mill were regular in shape and they are smaller in particle size and elongation than the particles pulverized by the Jet mill. Since the majority of the particles of phenytoin, which were pulverized by the LN2 bead mill, have the dimension of 1 μm or below, as shown in FIG. 2(B), it is found that the objective of pulverizing the material into submicron size has been attained by the ultra low temperature medium grinding with the LN2 bead mill, although it could not be attained by the conventional dry method for pulverization.

FIG. 29 shows a dry method particle size distribution that represents the effects of the rotating speed of the rotating shaft 2 on the particle size of pulverized phenytoin, while FIG. 30 shows a wet method particle size distribution that represents the effects of the rotating speed of the rotating discs 3 on the particle size of pulverized phenytoin. As stated above, the dry method particle size distribution was measured by the laser diffraction scattering method (Dry method), while the wet method particle size distribution was measured by the laser diffraction method (Wet method).

FIG. 31 shows a wet method particle size distribution that represents the effects of the diameter of the bead on the particle size of pulverized phenytoin. As stated above, this wet method particle size distribution was measured by the laser diffraction method (Wet method).

FIG. 32 represents the particle distribution of the bulk powder of phenytoin (OriB), the particle distribution of the phenytoin (Jet) pulverized by the dry method jet mill, and the particle distribution of the phenytoin (LN2) pulverized by the ultra low temperature medium grinding apparatus (LN2 bead mill) according to the present invention, wherein all the particle distributions were the results measured by the aforementioned dry method (Dry method). FIG. 33 represents the particle distribution of the bulk powder of phenytoin (OriB), the particle distribution of the phenytoin (Jet) pulverized by the dry method jet mill, and the particle distribution of the phenytoin (LN2) pulverized by the ultra low temperature medium grinding apparatus (LN2 bead mill) according to the present invention, wherein all the particle distribution were the results measured by the aforementioned wet method (Wet method). In both the measurement values of the dry method and the wet method, the particle distributions of the pulverized phenytoin (LN2) were broadened from approximately 0.3 μm to 10 μm, which were inconsistent with the electron micrographs (SEM). It is presumed that these measurement values were the results of measuring the sizes of the particles and the sizes of the aggregated particles contained therein. However, the percentage of the mass consisting of the particles having the size of 1 μm or below (the rate of submicron size particles) was measured up to 32% with regard to the particles pulverized by the wet method, which were three and a half times as much as the percentage figures measured as to the particles pulverized by the dry method, and thereby indicating excellent pulverizing effects of the wet method. When the diameter of zirconia bead is in the range of 0.3-1.0 mmØ, the effects of pulverization were substantially the same over the range. When the diameter of zirconia bead is 0.1 mmØ, however, a relatively inferior effect of pulverization was measured. From these measurement values, it is presumed that the results of pulverization depend not only upon the number of collisions among beads but also upon the force generated by the collision of a bead.

FIG. 34 represents the results of powder X-ray diffractometry (XRPD) of the original bulk of phenytoin (OriB), the phenytoin (Jet) pulverized by the dry method jet mill, and the phenytoin (LN2) pulverized by the ultra low temperature medium grinding apparatus (LN2 bead mill) according to the present invention, which were measured by a powder X-ray diffractometry device (RAD-2VC, Rigaku Corporation). FIG. 35 represents differential scanning calory of the original bulk of phenytoin (OriB), the phenytoin (Jet) pulverized by the dry method jet mill, and the phenytoin (LN2) pulverized by the ultra low temperature medium grinding apparatus (LN2 bead mill) according to the present invention, which were measured by a differential scanning calorimetry apparatus (DSC-60, SHIMADZU CORPORATION). As seen in the sample values attached to FIG. 35, the difference between ΔH value of the original bulk of phenytoin and ΔH value of the phenytoin (LN2) pulverized by the LN2 bead mill was very little, and crystalline descent was not found in the phenytoin (LN2) pulverized by the LN2 bead mill. On the other hand, the difference between ΔH value of the original bulk of phenytoin and ΔH value of the phenytoin (Jet) pulverized by the dry method jet mill was substantial, and it was found that the degree of crystallinity of the phenytoin (Jet) pulverized by the dry method jet mill was reduced to 81%. As described above, neither crystalline transformation nor crystalline descent was found in the phenytoin (LN2) before or after pulverized by the LN2 bead mill, so that it was found that the pulverization of phenytoin was processed with retaining the crystal form and crystalline of the phenytoin.

EXAMPLE 2

Figure 3A:
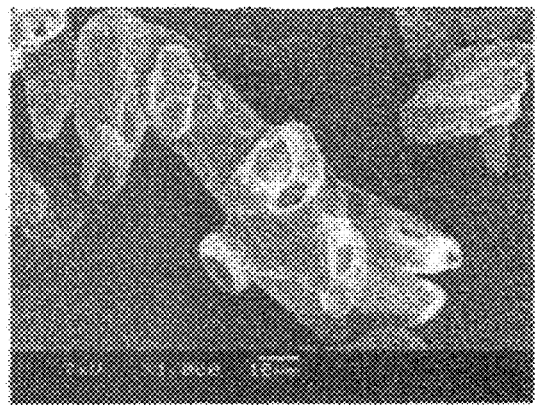
Figure 3B:
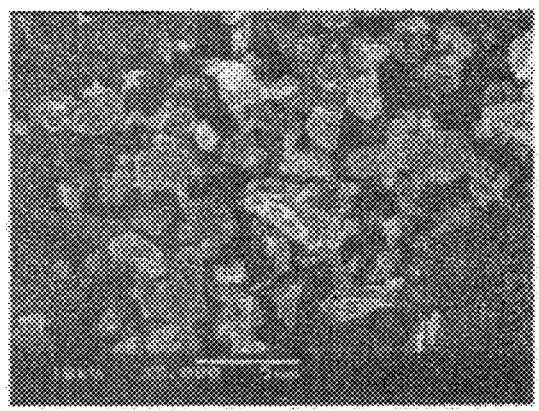
Figure 3C:

FIG. 3 shows electron micrographs (SEM) of the original bulk of ibuprofen and the pulverized particles of ibuprofen. Comparing FIG. 3(B) with FIG. 3(C), it was found that the particles pulverized by the LN2 bead mill were regular in shape and they are smaller in particle size and elongation than the particles pulverized by the Jet mill. It should be noted that the pulverization of low melting point material such as ibuprofen (76° C.) could be improved because the attack of heat generated at the time of pulverization could be modified immediately according to the present invention.

EXAMPLE 3

Figure 4:
Figure 4B:
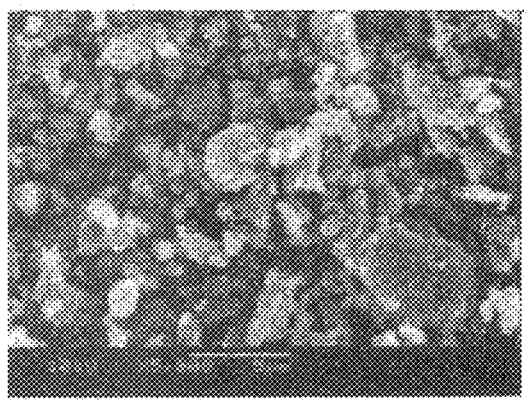
Figure 4C:

FIG. 4 shows electron micrographs (SEM) of the original bulk of salbutamol sulfate and the pulverized particles of salbutamol sulfate. Comparing FIG. 4(B) with FIG. 4(C), it was found that the particles pulverized by the LN2 bead mill were regular in shape and they are smaller in particle size and elongation than the particles pulverized by the Jet mill. It is also found that the method of the present invention is effective for the pulverization of water-soluble medicines such as salbutamol sulfate.

EXAMPLE 4

As an example of the present invention, the very low temperature medium grinding method according to the present invention may comprise the steps of: mixing additives such as dispersing agent with the original bulk and the like of pharmaceutical preparations; making a slurry that a mixture of the original bulk and the additives are suspended in a liquid nitrogen; and processing the slurry by a dry type very low temperature medium grinding method to pulverize the mixture of the original bulk and the additives into submicron sized particles or nano sized particles. In order to improve the solubility of low soluble medicines, the medicines have been pulverized into nano-sized particles to increase the superficial area thereof. When medicine was pulverized simply, however, the intensity of surface activity of the medicine increased just as much as the superficial area of the medicine had increased, so that it was observed that the pulverized particles of the medicine tended to agglutinate. The agglutinated particles decrease in solubility, so that the solubility of medicine might not be improved by the pulverization of medicine. In contrast, it is expected to prevent the original bulk from agglutinating by the method comprising the steps of: mixing the material such as original bulk of medicine with dispersing agent, pulverizing a mixture of the original bulk and dispersing agent by the ultra low temperature medium grinding method according to the present invention, and thereby obtaining pulverized particles between which the dispersing agent intervenes to prevent the agglutination. In addition, it is considered that the simultaneous pulverization of different materials, that is, the original bulk of medicine and the dispersing agent, further reduces particle diameters of the original bulk and the dispersing agent due to the difference between the physical property of the original bulk and that of the dispersing agent. As a result, the superficial area of the original bulk has further increased so that the original bulk is dispersed extremely rapidly in human body and the solubility of medicine can be improved drastically. Furthermore, the pulverized particles of medicine can be dispersed at an intended region of human body by selecting dispersing agent to ascertain the intended medicinal benefits. We prepared the first to third samples of fine powder and plotted the solubility of these samples against time on a graph. The first sample was prepared by pulverizing the original bulk of medicine by the ultra low temperature medium grinding method of the present invention. The second sample was prepared by pulverizing the original bulk of medicine and the dispersing agent individually by the ultra low temperature medium grinding method of the present invention and then, mixing the pulverized original bulk of medicine with the pulverized dispersing agent. The third sample was prepared by mixing the original bulk of medicine with the dispersing agent and then, pulverizing a mixture of the original bulk of medicine and the dispersing agent by the ultra low temperature medium grinding method of the present invention. Reviewing the graph, the solubility of the first sample increased gradually and in an approximately linear fashion as time advances. The solubility of the second sample increased relatively at a sharp angle in the early stages of dissolution and then, increased gradually to converge with the solubility value of approximately 1.3 times higher than the corresponding solubility value of the first sample. In contrast, the solubility of the third sample increased extremely rapidly to the solubility value of approximately 5 times higher than the corresponding solubility value of the second sample in the early stages of dissolution and then, increased in an arc to the solubility value of approximately 2 times higher than the corresponding solubility value of the second sample and then, increased gradually to the expected solubility value of 1.4 times higher the corresponding solubility value of the second sample. In the early stages of dissolution, the solubility of the first sample is approximately 1% and the solubility of the second sample is approximately 10%, however, the expected value of solubility of the third sample is 50 to 60%.

EXAMPLE 5

Phenytoin of a medical product chosen as a compound to be pulverized and Hypromellose-Acetate-Succinate (HPMCAS) chosen as an additive were mixed to prepare a mixture to be processed in this example, wherein the blend ratio of phenytoin to HPMCAS is 1:1 (weight ratio). 15 g of the mixture were pulverized in total amount and then, the improvement degree of solubility of the pulverized phenytoin, particularly the improvement degree of rate of dissolution of the pulverized phenytoin, was examined. The pulverization was performed under the condition that zirconium beads (the diameter of bead: 0.6 mm; the volume of beads: 150 cc) were used as pulverizing media, the rotating speed 1,600 rpm, and the pulverizing time 15 minutes. In addition, 6 liters of liquid nitrogen were used for removing the beads. The particle diameters of the pulverized phenytoin were shown in FIG. 36 (by evaluation of a dry aerial dispersion laser diffraction method; hereinafter evaluated by the same method).

EXAMPLE 6

By virtue of substantially the same processes and conditions as described in example 5, phenytoin was pulverized together with polyvinylpyrrolidone (PVP) that was used as additive. The particle diameters of the pulverized phenytoin were shown in FIG. 36.

EXAMPLE 7

By virtue of substantially the same processes and conditions as described in example 5, phenytoin was pulverized together with Methacrylic Acid Polymer (Eudragit L100) that was used as additive. The particle diameters of the pulverized phenytoin were shown in FIG. 36.

EXAMPLE 8

By virtue of substantially the same processes and conditions as described in example 5, phenytoin was pulverized together with carboxymethylcellulose (CMC) that was used as additive. The particle diameters of the pulverized phenytoin were shown in FIG. 36.

EXAMPLE 9

By virtue of substantially the same processes and conditions as described in example 5, phenytoin was pulverized together with microcrystalline cellulose (MCC) that was used as additive. The particle diameters of the pulverized phenytoin were shown in FIG. 36.

EXAMPLE 10

By virtue of substantially the same processes and conditions as described in example 5, phenytoin was pulverized together with low substituted hydroxy-propylcellulose (L-HPC) that was used as additive. The particle diameters of the pulverized phenytoin were shown in FIG. 36.

EXAMPLE 11

By virtue of substantially the same processes and conditions as described in example 5, phenytoin was pulverized together with hydroxypropyl-cellulose (HPMC) that was used as additive. The particle diameters of the pulverized phenytoin were shown in FIG. 36.

In FIG. 36, the item of nano % indicates a rate of pulverized particles having a diameter of 1 μm and below. The items of D10, D50 and D90 mean a particle diameter of 10%, 50% and 90% on an ogive curve, respectively. In addition, comparing with the result of the individual pulverization of phenytoin, a certain quantity of large particles was observed as a result of the concurrent pulverization of phenytoin and the additives except Methacrylic Acid Polymer (Eudragit L100). Those large particles may be observed for the reason that those additives are inherently hard-to-pulverized and some of the additives remain as large particles. As a consequence, the large particles magnify the entire particle size.

EXAMPLE 12

In order to verify the degree of improvement of solubility of the concurrently pulverized materials, which was obtained by concurrently pulverizing the test compound (phenytoin) made by example 5 and the additive (Hypromellose-Acetate-Succinate (HPMCAS)), the dissolution test was carried out as follows. A 33.3 mg sample of the pulverized materials was suspended in the water, which does not contain Tween80, to obtain a suspension. Then the suspension was put into a 900 mL test liquid (50 Mm phosphate buffer solution, pH6.8) and examined under the condition of 75 rpm in compliance with the pharmacopoeia second law (paddle method). The results of the examination are shown in FIG. 5.

REFERENCE EXAMPLE 1

A sample consisting of only a compound (phenytoin) to be pulverized was individually pulverized under the conditions shown in Example 5 to obtain a pulverized material, which was used to carry out the dissolution test as follows. A 66.7 mg sample of the pulverized material was suspended in the water, which contains a 0.1%(w/v) Tween80, to obtain a suspension. Then the suspension was put into the 900 mL test liquid and examined under the condition of 75 rpm in compliance with the pharmacopoeia second law (paddle method). As a result, it was found that the compound could be pulverized into the particles having a diameter of 0.1 μm or below by the individual pulverization, however, the pulverized particles agglutinate in the test liquid, so that the solubility of the pulverized particles was not improved, or rather became worse (Refer to FIG. 6).

REFERENCE EXAMPLE 2

Before the dissolution test of reference example 1 was carried out, the pulverized material prepared in reference example 1 was mixed with commercially available additives (lactose and L-HPC) in a vessel by hand. Then, the dissolution test was performed as for a mixture of the pulverized material and the additives. As a result of the dissolution test, it was found that the solubility of the compound was improved a little bit, however, the advantages of pulverization was not realized sufficiently (Refer to FIG. 7).

EXAMPLE 13

By virtue of substantially the same processes and conditions as described in example 12, the test compound (phenytoin) was concurrently pulverized together with polyvinylpyrrolidone (PVP) that was used as additive and then, the degree of improvement of solubility of the concurrently pulverized materials was verified. The test result is shown in FIG. 8.

EXAMPLE 14

By virtue of substantially the same processes and conditions as described in example 12, the test compound (phenytoin) was concurrently pulverized together with Methacrylic Acid Polymer (Eudragit L100) that was used as additive and then, the degree of improvement of solubility of the concurrently pulverized materials was verified. The test result is shown in FIG. 9.

EXAMPLE 15

By virtue of substantially the same processes and conditions as described in example 12, the test compound (phenytoin) was concurrently pulverized together with carboxymethylcellulose (CMC) that was used as additive and then, the degree of improvement of solubility of the concurrently pulverized materials was verified. The test result is shown in FIG. 10.

EXAMPLE 16

By virtue of substantially the same processes and conditions as described in example 12, the test compound (phenytoin) was concurrently pulverized together with microcrystalline cellulose (MCC) that was used as additive and then, the degree of improvement of solubility of the concurrently pulverized materials was verified. The test result is shown in FIG. 11.

EXAMPLE 17

By virtue of substantially the same processes and conditions as described in example 12, the test compound (phenytoin) was concurrently pulverized together with hydroxypropylcellulose (L-HPC) that was used as additive and then, the degree of improvement of solubility of the concurrently pulverized materials was verified. The test result is shown in FIG. 12.

EXAMPLE 18

By virtue of substantially the same processes and conditions as described in example 12, the test compound (phenytoin) was concurrently pulverized together with hydroxypropyl-cellulose (HPMC) that was used as additive and then, the degree of improvement of solubility of the concurrently pulverized materials was verified. The test result is shown in FIG. 13.

Judging from the test results stated above, the improvement of solubility of the concurrently pulverized materials according to the present invention is considered to depend upon the increase of effective superficial areas of the bulk material and the additives, which was caused by pulverizing the bulk material and the additives, and/or the increase of degree of wettability caused by the additives.

EXAMPLE 19

In this example, the solubility of the original bulk (phenytoin) to be pulverized and the solubility of a mixture of the original bulk (phenytoin) and commercially available additives (Eudragit L100, HPMC, PVP, MCC, L-HPC, CMC, HPMCAS) were measured. The solubility of the mixtures each were measured as follows: a 50 mg phenytoin and a 100 mg additive were put into a 900 mL test liquid (50 Mm, a phosphate buffer solution, pH6.8)(37° C.). After the solution was forcibly agitated at 250 rpm by a puddle, the concentration of phenytoin in the solution was measured at predetermined times. As a result, it was indicated that the solubility of the phenytoin pulverized with the additives were substantially the same as the solubility of the phenytoin pulverized without the additives. Consequently, it was found that the additives did not contribute to the improvement of solubility of the original bulk (phenytoin) (Refer to FIG. 14).

EXAMPLE 20

By virtue of substantially the same processes and conditions as described in example 12, the test compound (phenytoin) was concurrently pulverized together with an additive (PVP) and then, the solubility of concurrently pulverized phenytoin was verified. In this example, the test compound (phenytoin) and the additive (PVP) were also individually pulverized in a suspension and mixed with each other before vaporizing liquid nitrogen. Then the solubility of the individually pulverized phenytoin was verified. As a result, it was found that the solubility of the concurrently pulverized phenytoin was approximately the same as the solubility of the individually pulverized phenytoin (Refer to FIG. 15).

EXAMPLE 21

In this example, the test compound (phenytoin) was individually pulverized and mixed with commercially available additive (PVP) that was not pulverized. Then the solubility of the pulverized phenytoin was measured and compared with the solubility of the concurrently pulverized phenytoin (Example 13). As a result, it was found that the solubility of the individually pulverized phenytoin (this example) was not improved compared with the solubility of the concurrently pulverized phenytoin (example 13). It is assumed that it took time to dissolve the compound (phenytoin) because the particle size of the coexistent additive (PVP) was large (Refer to FIG. 16).

EXAMPLE 22

It is concerned that when a compound for medicine (phenytoin) is pulverized by the impact of zirconia beads, the zirconia beads are broken or worn away and the pulverized compound (phenytoin) is contaminated with the fragment of zirconia bead. Therefore, we measured the quantity of contamination of zirconia in the compound for medicine (phenytoin) when the compound (phenytoin) was pulverized by the impact of zirconia beads. The measurement was carried out under the basic pulverizing condition by use of zirconia beads (550 g, that is, 150 cc×3.66 g/cc). In addition, the preparation process for measurement comprises the steps of: adding phenytoin (0.1 g) as material to be pulverized to sulfuric acid; heating and dropping nitric acid to break down organic matter; verifying the complete dissolution by visual observation and then diluting by adding ultrapure water to become a given weight. The measurement was carried out by ICP-MS method (measuring mass number: Zr (90); analytical curve: 0, 1, 2, 5 ppb (A 1,000 ppm standard solution was diluted and used.). As a result of measurement, zirconium was 0.24 ppm (0.32 ppm as a quantity of zirconia). Considering that the residual quantity of common metals is 10 ppm, the quantity of zirconia is very little.

EXAMPLE 23

In order to verify a homogeneous mixing rate of a mixture in liquid nitrogen, phenytoin and polyvinylpyrrolidone (PVP) as an additive, both of which were not pulverized, were mixed in the weight ratio of 1:99 and in the weight ratio of 10:90, while the total weight of each of the mixtures was 15 g. The both mixtures were naturally dispersed in liquid nitrogen, respectively, and then the slurries each were stirred lightly to vaporize liquid nitrogen at room temperature. In each of the mixtures, in which phenytoin and polyvinylpyrrolidone (PVP) were mixed in the weight ratio of 1:99 and 10:90, ten samples of the mixture were taken from ten sites. Then the quantities of the compounds in each sample were measured. As a result, it was found that a highly homogeneous mixing could be realized in the mixtures and thereby, the effect of example 20 could be demonstrated. In FIGS. 37 and 38, RSD means a relative standard deviation value, which is preferably equal to or less than 5 to 6.

In FIG. 37, the homogeneous mixing rates of the mixture, in which phenytoin and polyvinylpyrrolidone (PVP) were mixed in the weight ratio of 1:99, are shown.

In FIG. 38, the homogeneous mixing rates of the mixture, in which phenytoin and polyvinylpyrrolidone (PVP) were mixed in the weight ratio of 10:90, are shown.

SUMMARY OF EXAMPLES 24-28

FIG. 17 illustrates the batch bead pulverizer Ready Mill RMB-04 (vessel volume 400 ml) manufactured by AIMEX Corporation, which was used in the following examples, and FIG. 18 illustrates a vertical section view of the vessel of the ready mill. Ready mill 11 is a vertical wet method medium agitator mill that comprises an electric motor and control unit assembly 13, which are fixed on a stand 12, and a vessel 14 detachably mounted on the assembly 13. As illustrated in FIG. 18, the vessel 14 is enclosed with a cooling jacket 15 and an upper opening of the vessel 14 is covered by a lid 16. A through-hole 17 is formed at a central portion of the lid 16 and a rotating shaft 18 is put into the through-hole 17. The rotating shaft 18 is driven by the electric motor of the assembly 13. A standard disc 13 is fixed on the rotating shaft 18 and the standard disc 13 comprising three discs arranged with a distance between adjacent discs. FIG. 19 is a photograph of the standard disc 13 taken from a side thereof. The standard disc assembly 13 is provided with a through-hole 19d, 19e, 19f and an agitating projection 19g, 19h, 19i that are formed on the disc 19a, 19b, 19c, respectively. The through-hole 19d, 19e, 19f each have openings on the upper and lower surfaces of the corresponding disc, while the agitating projection 19g, 19h, 19i each project downwardly from the lower surface of the corresponding disc. FIG. 20 is a photograph of a disc assembly having rotating wings taken from a side thereof, which comprises rotating wings that is substituted for the lowest disc 19e. The rotating wings of the disc assembly carry out the function of agitating the slurry accumulated in the vicinity of the bottom of the vessel 14 and moving the slurry upwardly in the vessel 14.

In order to pulverize and/or disperse original bulk by use of granular dry ice in a dispersing medium of liquid nitrogen in the ready mill 11, firstly, the vessel 14 and the standard disc assembly 19 or the aforementioned disc assembly having rotating wings are attached to the ready mill 11. Next, liquid nitrogen is poured into the vessel 14 and cooled down. After the cooling down, liquid nitrogen is poured again and then, the granular dry ice is put into the liquid nitrogen. And the slurry that has been prepared by suspending the original bulk in liquid nitrogen is poured into the vessel 14 whereby the preparation for pulverization and/or dispersion of the original bulk is completed. Then the rotating shaft 18 of the ready mill 11 is driven to rotate the standard disc assembly 19 or the disc assembly with rotating wings and agitate the slurry in the vessel 14. Thereby, the granular dry ice works on the particles of original bulk to pulverize the particles into a desired particle size and/or disperse agglomerated particles of original bulk that might exist in the slurry. In addition, a proportionate amount of liquid nitrogen has to be added to the vessel 14 according to the pulverization time by the end of pulverization because liquid nitrogen is vaporized during the pulverization. In order to determine the replenishment time and quantity of liquid nitrogen, the weight of the vessel 14 is continuously measured by a load cell whereby the liquid level control of liquid nitrogen is carried out. In the following examples, the pulverization was carried out by controlling the weight of the vessel 14 within the range of ±10 g on the basis of the weight of the vessel 14 at the time of immediately after commencing pulverization.

EXAMPLE 24

Preparation of Granular Dry Ice

In order to confirm as to whether granular dry ice having a desired particle diameter can be produced or not, dry ice particles were pulverized in liquid nitrogen by use of aforementioned ready mill 11. The dry ice particles having reasonable diameters were independently pulverized in liquid nitrogen by the ready mill 11 to which the standard disc assembly 19 was attached. Table 31 represents the particle sizes of dry ice before pulverization, which were measured at 210 sites of the granular dry ice. Table 32 represents the particle sizes of dry ice after the dry ice particles were agitated in liquid nitrogen for 120 minutes, which were measured at 200 sites of the agitated dry ice.

As shown in FIG. 39, the average diameter of the dry ice particles before they were pulverized is 375.4 μm, wherein the average value of the maximum diameters of the dry ice particles is 648.9 μm and the average value of the minimum diameters of the dry ice particles is 169.6 μm. FIG. 21 shows a photograph of the particles of dry ice taken by a digital type optical microscope at 100× magnifications before they are pulverized. In addition, as shown in FIG. 40, the average diameter of the dry ice particles after they were pulverized is 266.5 μm, wherein the average value of the maximum diameters of the dry ice particles is 452.1 μm and the average value of the minimum diameters of the dry ice particles is 114.0 μm. FIG. 22 shows a photograph of the pulverized particles of dry ice taken by a digital type optical microscope at 100× magnifications. From FIG. 39, FIG. 40, FIG. 21 and FIG. 22, it can be confirmed that the particle diameters of dry ice particles can be reduced by individually pulverizing dry ice particles in liquid nitrogen in the ready mill 11. The digital type optical microscope is Digital Microscope VHX-500 manufactured by KEYENCE CORPORATION.

As stated above, the dry ice particles can be also produced by the steps of: filling liquid nitrogen in a liquefied gas storage container, putting dry ice particles such as "Shot Dry" for shot blasting into the liquid nitrogen, and soaking the dry ice particles in the liquid nitrogen for 12 hours, wherein the liquid nitrogen and the dry ice particles are mixed so that the volume ratio of the liquid nitrogen to the dry ice particles should be 2:1. After the dry ice particles have been soaked in the liquid nitrogen for 12 hours, granular dry ice can be obtained by separating the liquid nitrogen. The granular dry ice produced can be used as dry ice beads for pulverizing materials. When cylindrical dry ice particles for shot blasting (Shot Dry), which are, for example, 3.0 mm in diameter and 5.0 to 30.0 mm in length, are soaked in liquid nitrogen for 12 hours according to the method for producing granular dry ice, the granular dry ice having the average particle diameter of 0.5 to 1.5 mm is produced.

EXAMPLE 25

Recovery Percentage of Pulverized Material

When putting liquid nitrogen into the vessel 4 of the batch bead pulverizer Ready Mill RMB-04 (vessel volume 400 ml) manufactured by AIMEX Corporation, pouring in a 150 ml dry ice having the average particle diameter of 0.5 mm and a 15 g phenytoin in the liquid nitrogen, and agitating the slurry by the standard disc assembly 19, the recovered phenytoin was 13.18 g and the recovery percentage of phenytoin was 87%. The unrecovered phenytoin was vaporized from the vessel 14 to the atmosphere during the process for pulverization. When pulverizing phenytoin under the same conditions as mentioned above, except zirconia bead having a diameter of 0.6 mm was substituted for the dry ice, the recovered phenytoin was 5.36 g and the recovery percentage of phenytoin was 35%. The recovery percentage of phenytoin by use of dry ice should be compared with the recovery percentage of phenytoin by use of zirconia beads.

EXAMPLE 26

Pulverizing Phenytoin

In compliance with the method for producing fine powder according to the present invention, phenytoin particles were pulverized by use of the batch bead pulverizer Ready Mill RMB-04 (vessel volume 400 ml) manufactured by AIMEX Corporation, to which the standard disc assembly 19 was attached.

The experimental conditions are as follows:
(1) Vertical medium agitating mill: vessel volume 0.4 liter; standard disc assembly of three discs each having a diameter of 55 mm and a thickness of 5 mm
(2) Peripheral velocity of disc of the standard disc assembly: 8.05 m/s
(3) Pulverizing time: from 30 minutes to 120 minutes
(4) Volume of dry ice: 150 cc
(5) Weight of phenytoin: 15 g The size of pulverized particles of phenytoin was measured by a particle size measurement apparatus SALD-2100 manufactured by SHIMADZU CORPORATION. The measured distribution of particle size is shown in FIG. 41 and the average particle diameter is shown in FIG. 42.

FIG. 23 is a photograph of an electron microscope (at 10000× magnifications) of the phenytoin pulverized by the method for producing fine powder according to the present invention for 30 minutes. FIG. 24 is a photograph of an electron microscope (at 10000× magnifications) of the phenytoin pulverized by the method for producing fine powder according to the present invention for 60 minutes. FIG. 25 a photograph of an electron microscope (at 10000× magnifications) of the phenytoin pulverized by the method for producing fine powder according to the present invention for 120 minutes. Although a coarse particle CP1 is observed in the photograph of FIG. 23, any particles having the size equivalent to CP1 are not found in the photographs of FIGS. 24 and 25. Thereby, the pulverization of the particles of phenytoin was progressed as the time for pulverizing advances. FIG. 26 is a photograph of the mixture of phenytoin and dry ice particles, taken by a digital type optical microscope (at 100× magnifications), after pulverizing phenytoin for 30 minutes by means of granular dry ice in compliance with the method for producing fine powder according to the present invention and then vaporizing liquid nitrogen. Those electron micrographs were taken by a scanning electron microscope JSM-6060 manufactured by JEOL LTD. In addition, the aforementioned digital type optical micrographs were taken by Digital Microscope VHX-500 manufactured by KEYENCE CORPORATION.

Judging from FIG. 41, FIG. 42, FIGS. 23-26, it is found that phenytoin is pulverized by dry ice particles in compliance with the method of the present invention.

EXAMPLE 27

Pulverizing Indomethacin

In compliance with the method for producing fine powder according to the present invention, indomethacin particles were pulverized by use of the batch bead pulverizer Ready Mill RMB-04 (vessel volume 400 ml) manufactured by AIMEX Corporation, to which the standard disc assembly 19 was attached.

The experimental conditions are as follows:
(1) Vertical medium agitating mill: vessel volume 0.4 liter; standard disc assembly of three discs each having a diameter of 55 mm and a thickness of 5 mm
(2) Peripheral velocity of disc of the standard disc assembly: 8.05 m/s
(3) Pulverizing time: from 30 minutes to 120 minutes
(4) Volume of dry ice: 150 cc
(5) Weight of indomethacin: 15 g The size of pulverized particles of indomethacin was measured by a particle size measurement apparatus SALD-2100 manufactured by SHIMADZU CORPORATION. The measured distribution of particle size of indomethacin is shown in FIG. 43 and the average particle diameter is shown in FIG. 44.

FIG. 27 is an electron micrograph (at 10000× magnifications) of indomethacin pulverized for 60 minutes in compliance with the method for producing fine powder according to the present invention. FIG. 28 is an electron micrograph (at 1000× magnifications) of indomethacin pulverized for 120 minutes in compliance with the method for producing fine powder according to the present invention. Although a coarse particle CP1 is observed in the photograph of FIG. 27, any particles having the size equivalent to CP1 are not found in the photograph of FIG. 28. Thereby, the pulverization of the particles of indomethacin was progressed as the time for pulverizing advances. Those electron micrographs were taken by a scanning electron microscope JSM-6060 manufactured by JEOL LTD.

EXAMPLE 28

Concurrently Pulverizing Phenytoin and Polyvinylpyrrolidone (PVP)

In compliance with the method for producing fine powder according to the present invention, phenytoin 7.5 g and polyvinylpyrrolidone (PVP) 7.5 g were concurrently pulverized by use of dry ice beads in the batch bead pulverizer Ready Mill RMB-04 (vessel volume 400 ml) manufactured by AIMEX Corporation, to which the standard disc assembly 19 was attached. The results of the concurrently pulverizing are shown in FIG. 45.

The experimental conditions are as follows:
(1) Vertical medium agitating mill: vessel volume 0.4 liter; standard disc assembly of three discs each having a diameter of 55 mm and a thickness of 5 mm
(2) Peripheral velocity of disc of the standard disc assembly: 8.05 m/s
(3) Pulverizing time: from 30 minutes to 120 minutes
(4) Volume of dry ice: 150 cc
(5) Weight of phenytoin: 7.5 g
(6) Weight of polyvinylpyrrolidone (PVP): 7.5 g In FIG. 45, the item of quantitative value (%) indicates a ratio of phenytoin composition included in concurrently pulverized materials to feed composition. If the quantitative value is equal to or more than 90%, the pulverizing process is of practical use. From FIG. 45, it is found that the quantitative value (%) obtained from the samples pulverized by dry ice beads is far higher than the quantitative value (%) obtained from the sample pulverized by zirconia beads.

The above experiment used the batch bead pulverizer Ready Mill RMB-04 (vessel volume 400 ml) manufactured by AIMEX Corporation, to which the standard disc assembly 19 was attached. In addition to the above experiment, phenytoin 7.5 g and polyvinylpyrrolidone (PVP) 7.5 g were concurrently pulverized by use of dry ice beads in the batch bead pulverizer Ready Mill RMB-04 (vessel volume 400 ml) manufactured by AIMEX Corporation, wherein the disc assembly having rotating wings as shown in FIG. 20 was substituted for the standard disc assembly 19. As a result of this concurrent pulverization, it was found that the combination of the dry ice beads and the disc assembly having rotating wings significantly contributed to the enhancement of solubility as shown in FIG. 46. Since the disc assembly with rotating wings produces such an excellent stirring effect for enhancing the pulverization of materials, it is observed from FIG. 46 that the solubility of approximately 90% could be attained at the pulverization time of 60 minutes.

As a result of concurrently pulverizing phenytoin and polyvinylpyrrolidone (PVP) by using a combination of the dry ice beads and the disc assembly with rotating wings, it was also found that the quantitative value (%) and the RSD value (relative standard deviation), which indicates dispersion of measured values, were also high as the solubility was high. As the RSD value (relative standard deviation) reduces, the degree of homogeneous mixing of phenytoin and PVP increases. In general, it is considered that the degree of homogeneous mixing may be at practical level if the RSD value would be approximately equal to or less than 5.0%. In addition, the quantitative value (%) indicates the ratio of phenytoin composition included in the concurrently pulverized materials to feed composition. It is also considered that the degree of homogeneous mixing may be at practical level if the quantitative value would be equal to or more than 90%. It is found from FIG. 47 that the dry ice beads effectively stirred by the disc assembly with rotating wings enhance the mixing of phenytoin and PVP.

INDUSTRIAL APPLICABILITY

The present invention is not limited to the application to pulverization of medicine and is applicable to a broad range of technology such as cosmetics, toner, water base paint, materials for LCD displays, parts of digital cameras, recording medium, materials of solar batteries, parts of cellular phones, substrates, parts of electric automobiles, thermosensitive enamel paper, and development of DDS (Drug Delivery System).

INDICATION OF REFERENCE NUMERALS

1: vessel
2: rotating shaft
3: disc
4: beads
11: vertical wet method medium agitating mill
14: vessel
18: rotating shaft
19: standard disc assembly
19a, 19b, and 19c: disc

What is claimed is:

1. A method for producing homogeneously mixed fine powder, comprising the steps of:
suspending a first material selected from a drug substance or active pharmaceutical ingredient (API) and an additive for medicines in a liquefied inert gas to form a first slurry in one vessel and suspending a second material selected from a drug substance or active pharmaceutical ingredient (API) and an additive for medicines, but is different from said first material, in a liquefied inert gas to form a second slurry in another vessel;
putting grinding media in said first slurry and said second slurry;
stirring said first slurry together with said grinding media in said one vessel so that relative movements are generated between said grinding media and thereby said first material is individually pulverized into first particles in said first slurry as the results of impact and shear forces received from said grinding media; and
stirring said second slurry together with said grinding media in said another vessel so that relative movements are generated between said grinding media and thereby said second material is individually pulverized into second particles in said second slurry as the results of impact and shear forces received from said grinding media;
removing said grinding media from said first and second slurries and then mixing said first slurry with said second slurry to produce a mixture of said first slurry and said second slurry where said first particles and said second particles are suspended; and
stirring the mixture of said first slurry and said second slurry at room temperature to produce a homogeneous mixture of said first particles and said second particles in the mixture of said first slurry and said second slurry, and then vaporizing said liquefied inert gas in the mixture of said first and second slurries to recover the homogeneous mixture of said first particles and said second particles.

2. The method as recited in claim 1, wherein said additive for medicines is a substance selected from the group consisting of Hypromellose-Acetate-Succinate (HPMCAS), polyvinylpyrrolidone (PVP), Methacrylic Acid Polymer (Eudragit L100), carboxymethylcellulose (CMC), microcrystalline cellulose (MMC), low substituted hydroxy-propylcellulose (L-HPC), hydroxypropyl-cellulose (HPMC), and lactose.

3. The method as recited in claim 1, wherein said liquefied inert gas is liquid nitrogen, liquid helium, liquid neon, liquid argon, liquid krypton, or liquid xenon.

4. The method as recited in claim 1, wherein said grinding medium is a plurality of beads of zirconia, agate, quarts, titania, tungsten carbide, silicon nitride, alumina, stainless steel, soda glass, low soda glass, soda less glass, high density glass, dry ice (solid carbon dioxide) or solid nitrous oxide.

5. The method as recited in claim 4, wherein said grinding medium is a plurality of beads of said dry ice (solid carbon dioxide) and wherein said first material is pulverized into submicron-sized and/or nano-sized particles by the beads of dry ice, while the particle diameter of said beads of dry ice reduces as the pulverization of said material proceeds.

6. The method as recited in claim 1, wherein said liquefied inert gas is at least one liquefied gas selected from the group of liquid nitrogen, liquid helium, liquid neon, liquid argon, liquid krypton, and liquid xenon.

7. The fine powder made of a homogeneous mixture of said first particles of said first materials and said second particles of said second materials produced by the method as recited in claim 1.

8. A method for producing granular dry ice particles suitable for grinding medium for a pulverizer, comprising the steps of:
putting cylindrical dry ice particles, each 3.0 mm in diameter and 5.0 to 10.0 mm in length, into liquid nitrogen that is preserved in a liquefied gas container, wherein the ratio of the volume of said liquid nitrogen to the volume of said cylindrical dry ice particles is 2:1;
soaking said cylindrical dry ice particles in said liquid nitrogen for approximately 12 hours to transform said cylindrical dry ice particles into granular dry ice particles having an average particle diameter of 0.5 to 1.5 mm; and
separating said granular dry ice particles from said liquid nitrogen.

* * * * *